US008864673B2

(12) United States Patent
Miyake

(10) Patent No.: US 8,864,673 B2
(45) Date of Patent: Oct. 21, 2014

(54) ULTRASOUND DIAGNOSTIC APPARATUS WITH ELECTRICAL IMPEDANCE MATCHING

(71) Applicant: Olympus Medical Systems Corp., Tokyo (JP)

(72) Inventor: Tatsuya Miyake, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/920,614

(22) Filed: Jun. 18, 2013

(65) Prior Publication Data

US 2013/0331703 A1    Dec. 12, 2013

Related U.S. Application Data

(63) Continuation of application No. PCT/JP2013/051167, filed on Jan. 22, 2013.

(30) Foreign Application Priority Data

Feb. 1, 2012  (JP) .................. 2012-019998

(51) Int. Cl.
*A61B 8/00* (2006.01)
*A61B 8/12* (2006.01)

(52) U.S. Cl.
CPC .............. *A61B 8/4494* (2013.01); *A61B 8/12* (2013.01); *A61B 8/4444* (2013.01)
USPC ........................................... 600/459

(58) Field of Classification Search
CPC ...... A61B 8/44; A61B 8/4444; A61B 8/4494; G01S 15/8906
USPC ........................................... 600/459
See application file for complete search history.

(56) References Cited

U.S. PATENT DOCUMENTS 4,712,112 A * 12/1987 Carr ............................. 343/788
5,298,828 A *  3/1994 Radovanovich ............... 310/319

(Continued)

FOREIGN PATENT DOCUMENTS

EP       600654 A1 *  6/1994
EP    1 504 721 A1     2/2005

(Continued)

OTHER PUBLICATIONS

English abstract only of WO 2005/120360 A1 dated Dec. 22, 2005.

*Primary Examiner* — Rajeev Siripurapu
(74) *Attorney, Agent, or Firm* — Scully, Scott, Murphy & Presser, P.C.

(57) ABSTRACT

An ultrasound diagnostic apparatus includes: an ultrasound probe including a capacitive micromachined ultrasound transducer; an ultrasound observation apparatus, and a reception circuit; a transmission ultrasound transducer and a reception ultrasound transducer included in the capacitive micromachined ultrasound transducer, the transmission ultrasound transducer including a plurality of transmission capacitive cells, and the reception ultrasound transducer including a plurality of reception capacitive cells; a transmission signal cable connecting the transmission ultrasound transducer and the transmission circuit; a reception signal cable connecting the reception ultrasound transducer and the reception circuit; a first matching section and a second matching section that perform electrical impedance matching for the ultrasound transmission signal and the ultrasound reception signal, the first matching section and the second matching section being provided for a predetermined transmission region and a predetermined reception region for generating an ultrasound beam for one pixel, respectively.

15 Claims, 10 Drawing Sheets

(56) References Cited

U.S. PATENT DOCUMENTS

| | | | |
|---|---|---|---|
| 5,706,816 A * | 1/1998 | Mochizuki et al. | 600/443 |
| 7,044,915 B2 * | 5/2006 | White et al. | 600/459 |
| 2002/0157472 A1 * | 10/2002 | Stephens et al. | 73/626 |
| 2005/0256402 A1 | 11/2005 | Kawashima et al. | |
| 2007/0164632 A1 | 7/2007 | Adachi et al. | |
| 2008/0139946 A1 | 6/2008 | Adachi et al. | |
| 2009/0048522 A1 * | 2/2009 | Huang | 600/459 |
| 2011/0130663 A1 * | 6/2011 | Raju et al. | 600/459 |

FOREIGN PATENT DOCUMENTS

| | | |
|---|---|---|
| EP | 1 761 104 A | 3/2007 |
| EP | 2 042 102 A1 | 4/2009 |
| JP | 06-225881 A | 8/1994 |
| JP | 2001-074710 A | 3/2001 |
| JP | 2003-135464 A | 5/2003 |
| JP | 2004-097588 A | 4/2004 |
| JP | 2004-113628 A | 4/2004 |
| JP | 2004-141672 A | 5/2004 |
| JP | 2005-177205 A | 7/2005 |
| JP | 2009-194934 A | 8/2009 |
| JP | 2009-239976 A | 10/2009 |
| JP | 4347885 B | 10/2009 |
| JP | 4575372 | 11/2010 |
| WO | WO 2004/028375 A1 | 4/2004 |
| WO | WO 2005/120130 A1 | 12/2005 |

* cited by examiner

ULTRASOUND DIAGNOSTIC APPARATUS WITH ELECTRICAL IMPEDANCE MATCHING

CROSS REFERENCE TO RELATED APPLICATION

This application is a continuation application of PCT/JP2013/051167 filed on Jan. 22, 2013 and claims benefit of Japanese Application No. 2012-019998 filed in Japan on Feb. 1, 2012, the entire contents of which are incorporated herein by this reference.

BACKGROUND OF THE INVENTION

1. Field of the Invention

The present invention relates to an ultrasound diagnostic apparatus that performs ultrasound diagnosis using a capacitive micromachined ultrasound transducer.

2. Description of the Related Art

In recent years, the development of ultrasound devices using a capacitive micromachined ultrasound transducer (abbreviated as "C-MUT"), which is different from a piezoelectric transducer, as an ultrasound transducer has been advanced.

In the C-MUT, a vacuum space region is provided between upper and lower electrodes, and a DC bias voltage and a transmission signal or an ultrasound transmission signal are applied to the upper electrode to send ultrasound out toward a site to be examined, and ultrasound returned as a result of reflection is received by an upper film, converted into an ultrasound echo signal (referred to as "ultrasound reception signal" or simply as "reception signal") as a converted electric signal, and used for ultrasound examination or diagnosis.

The transmission signal transmitted to the C-MUT and the reception signal received in the C-MUT are conveyed via respective cables, and here, the problem of an impedance mismatch may arise between the cables and capacitances the C-MUT has, resulting in a decrease in transmitting/receiving sensitivity.

More specifically, reflection of the transmission signal due to an impedance mismatch causes distortion of the waveform of the transmission signal, a decrease in level of a transmission signal that can actually be applied to the C-MUT or superimposition of a waveform arising from the mismatch on the received reception signal, resulting in a decrease in receiving sensitivity and/or S/N ratio.

Addressing such phenomena, the related art in Japanese Patent No. 4575372 clearly indicates including impedance converting means for converting an output of a transducer element so as to have a low impedance for electrical impedance matching with an impedance of a cable, in the vicinity of the transducer element, for prevention of a decrease in receiving sensitivity.

In the above related art, a same route is provided for transmission and reception, and in particular, focusing on a received signal output, the impedance converting means is provided.

SUMMARY OF THE INVENTION

An ultrasound diagnostic apparatus according to an aspect of the present invention includes: an ultrasound probe including a capacitive micromachined ultrasound transducer; an ultrasound observation apparatus to which the ultrasound probe is detachably connected, the ultrasound observation apparatus including a transmission circuit that generates an ultrasound transmission signal for sending ultrasound out from the capacitive micromachined ultrasound transducer, and a reception circuit that performs signal processing on an ultrasound reception signal generated as a result of ultrasound being received by the capacitive micromachined ultrasound transducer; a transmission ultrasound transducer and a reception ultrasound transducer included in the capacitive micromachined ultrasound transducer, the transmission ultrasound transducer including a plurality of transmission capacitive cells that each send ultrasound out, and the reception ultrasound transducer including a plurality of reception capacitive cells that each receive reflected ultrasound of the sent-out ultrasound and output an ultrasound reception signal; a transmission signal cable connecting the transmission ultrasound transducer and the transmission circuit in the ultrasound observation apparatus; a reception signal cable connecting the reception ultrasound transducer and the reception circuit in the ultrasound observation apparatus; and a first matching section and a second matching section that perform electrical impedance matching for the ultrasound transmission signal conveyed via the transmission signal cable and the ultrasound reception signal conveyed via the reception signal cable, respectively, and the capacitive micromachined ultrasound transducer is configured in such a manner that the plurality of transmission capacitive cells are arranged in a predetermined transmission region set as a transmission region from which ultrasound for generating an ultrasound beam for one pixel is transmitted, and the plurality of reception capacitive cells are arranged in a predetermined reception region set as a reception region in which reflected ultrasound of ultrasound transmitted from the predetermined transmission region is received in order to obtain an ultrasound beam for one pixel, and the first matching section and the second matching section are provided for each of the predetermined transmission region and the predetermined reception region, respectively.

DETAILED DESCRIPTION OF THE PREFERRED EMBODIMENTS

Embodiments of the present invention will be described below with reference to the drawings.

(First Embodiment)

Figure 1:
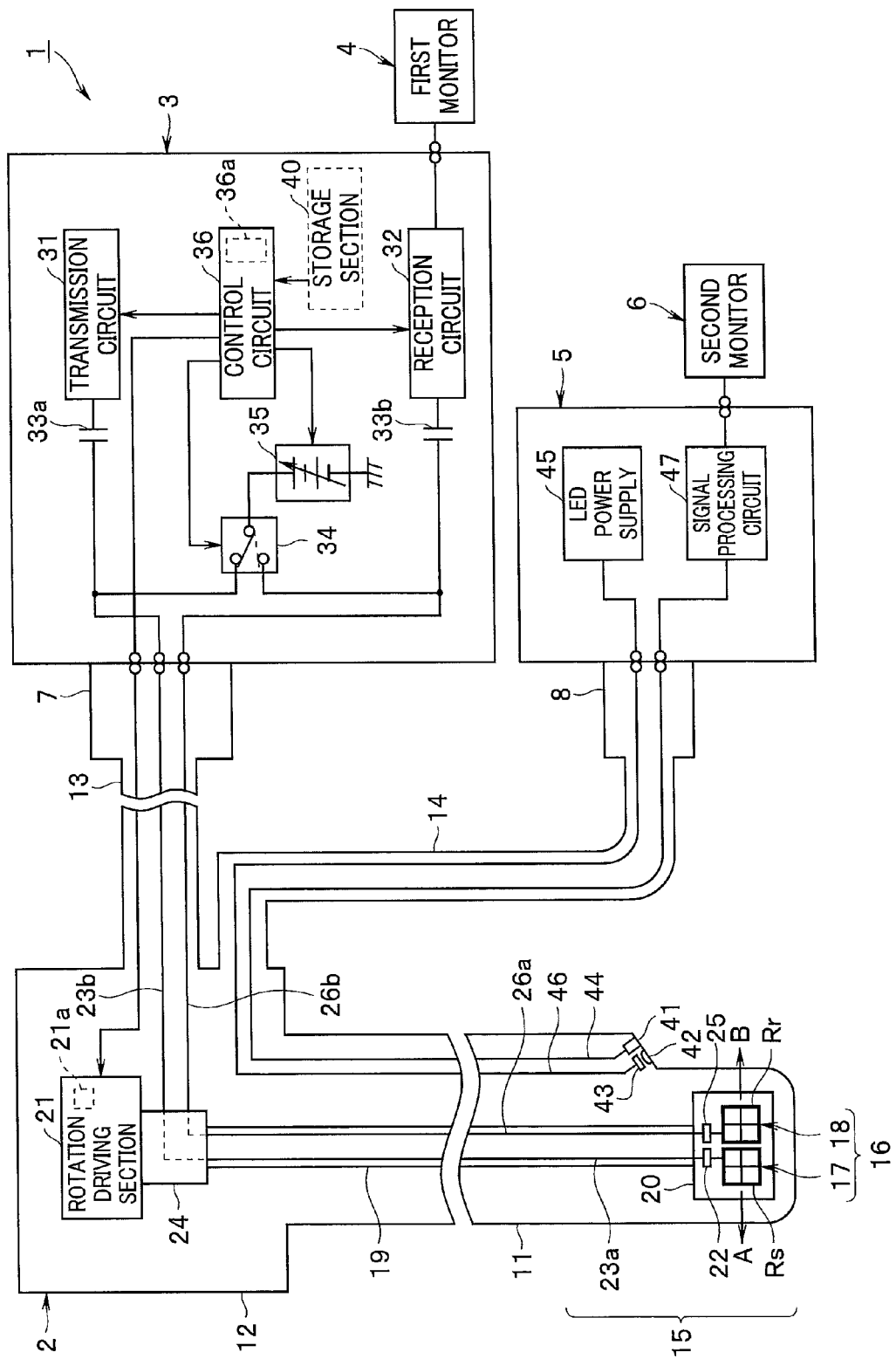
FIG. 1 is a diagram illustrating an overall configuration of an ultrasound diagnostic apparatus according to a first embodiment of the present invention.

As illustrated in FIG. 1, an ultrasound diagnostic apparatus 1 according to a first embodiment of the present invention includes: an ultrasound endoscope 2, a ultrasound observation apparatus (hereinafter simply abbreviated as "observation apparatus") 3 to which an ultrasound connector 7 of the ultrasound endoscope 2 is detachably attached (connected); a first monitor 4 that displays an ultrasound tomographic image generated by the observation apparatus 3; an endoscope processor 5 to which an endoscope connector 8 of the ultrasound endoscope 2 is detachably attached (connected); and a second monitor 6 that displays an endoscopic image generated by the endoscope processor 5.

The ultrasound endoscope 2 includes an insertion portion 11 to be inserted into a body cavity, an operation portion 12 provided at a rear end of the insertion portion 11, an ultrasound cable 13 extending from the operation portion 12, and an endoscope cable 14. At a terminal of the ultrasound cable 13, the ultrasound connector 7 is provided and at a terminal of the endoscope cable 14, the endoscope connector 8 is provided.

Inside a distal end portion 15 of the insertion portion 11, a capacitive micromachined ultrasound transducer (C-MUT) 16 that sends out (transmits) ultrasound and receives ultrasound returning as a result of the sent-out ultrasound being reflected is provided, and the C-MUT 16 is attached to a distal end of a rotatable shaft 19 inserted in the insertion portion 11, via a transducer mount 20.

In the present embodiment, the C-MUT 16 includes a transmission ultrasound transducer 17 including a plurality of (here, four) transmission capacitive micromachined ultrasound transducer cells (hereinafter, "transmission capacitive cells") 17a to 17d that each send out ultrasound upon application of an ultrasound transmission signal thereto, and a reception ultrasound transducer 18 including a plurality of (here, four) reception capacitive micromachined ultrasound transducer cells (hereinafter, "reception capacitive cells") 18a to 18d that each receive ultrasound returned as a result of reflection and output an ultrasound reception signal.

Since the reception ultrasound transducer 18 receives ultrasound resulting from ultrasound sent out by the transmission ultrasound transducer 17 being reflected by a site to be examined, the transmission ultrasound transducer 17 and the reception ultrasound transducer 18 are desirably arranged within a small distance, and in FIG. 1, the transmission ultrasound transducer 17 and the reception ultrasound transducer 18 are arranged in a transmission C-MUT cell region (abbreviated as "transmission cell region") Rs and a reception C-MUT cell region (abbreviated as "reception cell region") Rr, respectively, which are a predetermined transmission region and a predetermined reception region formed adjacent to each other in the distal end portion 15.

In the present embodiment, the transmission cell region Rs in which the four transmission capacitive cells 17a to 17d are arranged serves as a predetermined transmission region from which ultrasound for generating an ultrasound beam for one pixel is transmitted in each transmission period for a case where an ultrasound image for one frame in radial scanning is obtained, for example, as described below. In other words, the four transmission capacitive cells 17a to 17d are arranged in the transmission cell region Rs, which is a predetermined transmission region set as a transmission region from which ultrasound for generating an ultrasound beam for one pixel is transmitted.

Also, the reception cell region Rr in which the four reception capacitive cells 18a to 18d are arranged serves as a predetermined reception region in which ultrasound for generating an ultrasound beam for one pixel is received in each reception period for a case where an ultrasound image for one frame in radial scanning is obtained. In other words, the four reception capacitive cells 18a to 18d are arranged in the reception cell region Rr, which serves as a predetermined reception region set as a reception region in which reflected ultrasound (reflected signals) of the ultrasound transmitted from the four transmission capacitive cells 17a to 17d arranged in the transmission cell region Rs is received in order to obtain ultrasound beams for one pixel.

Figure 2:
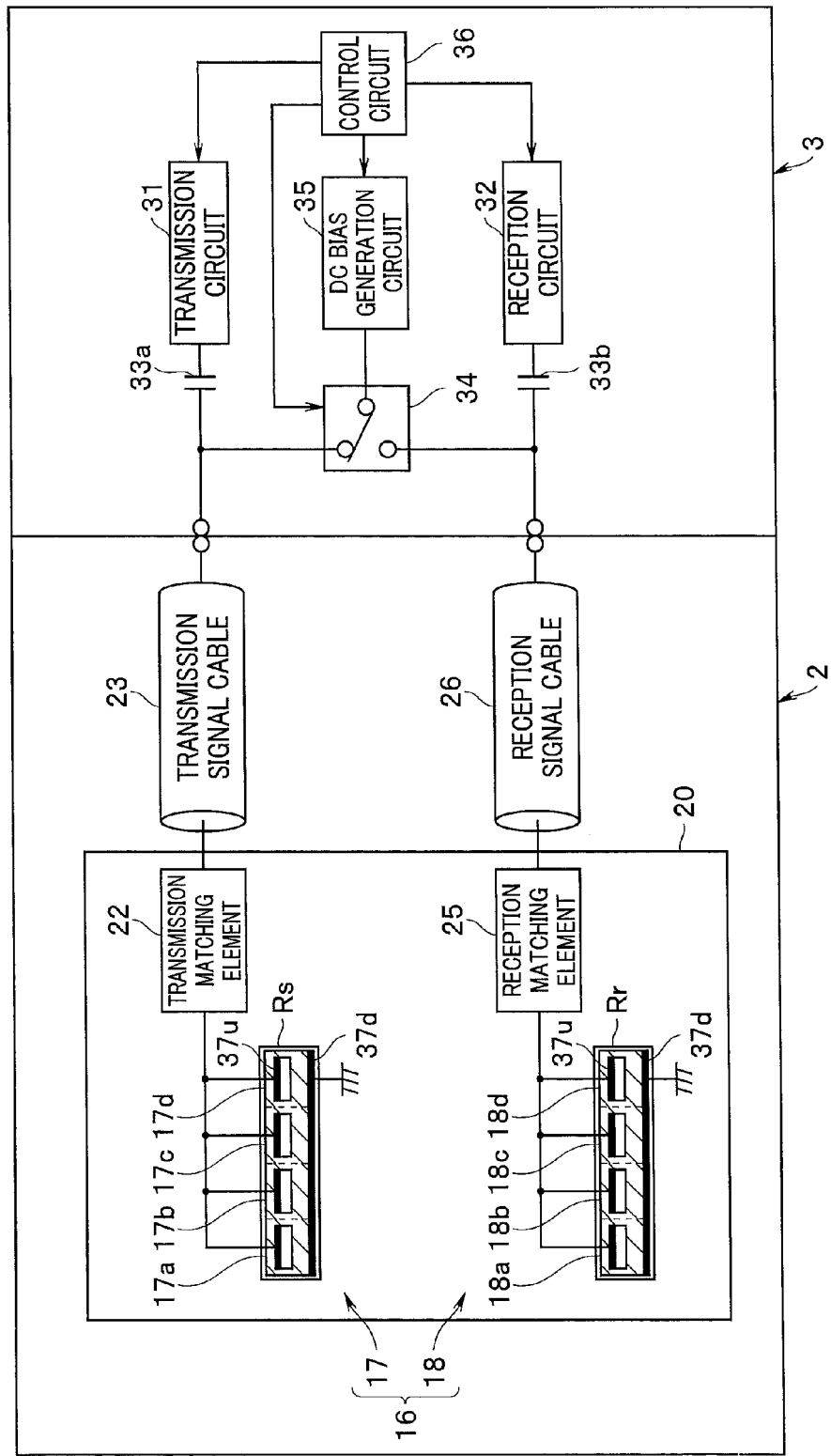
FIG. 2 is a block diagram illustrating a configuration of a circuit system that transmits/receives ultrasound in FIG. 1.
Figure 3:
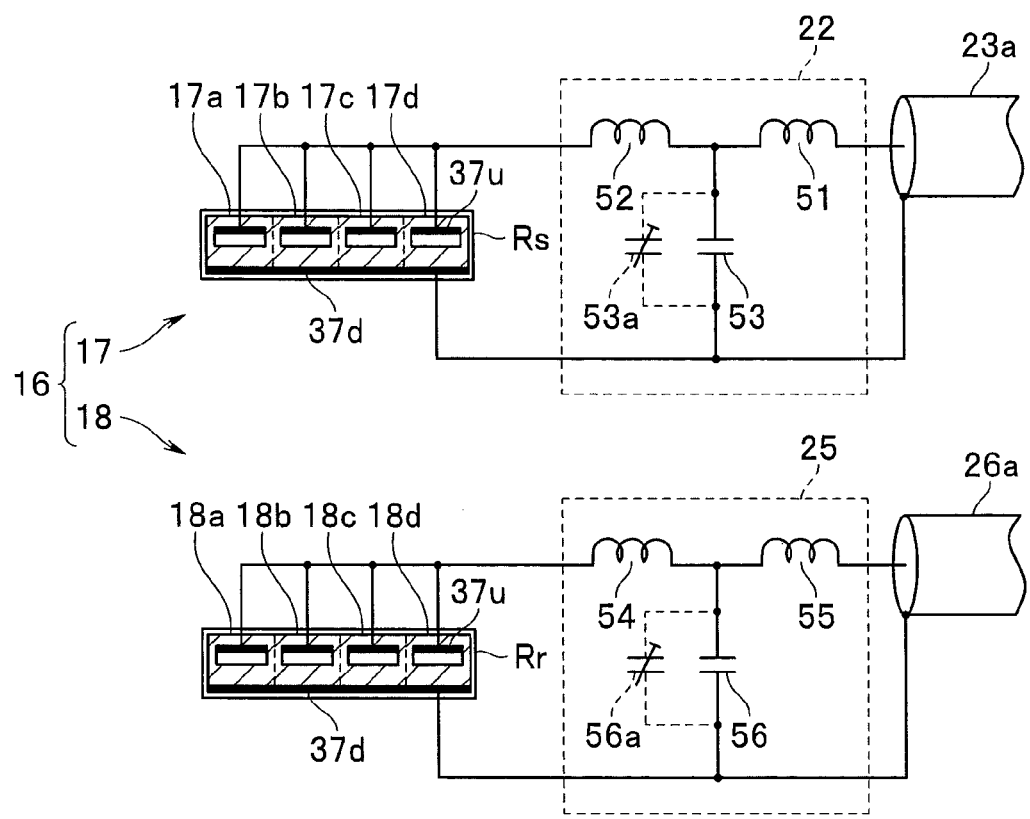
FIG. 3 is a circuit diagram illustrating specific circuits in matching elements.

Note that in FIG. 1, illustration of reference numerals of the transmission capacitive cells 17a to 17d and the reception capacitive cells 18a to 18d are omitted (see FIG. 2 or 3). Also, a center of the transmission cell region Rs in which the four transmission capacitive cells 17a to 17d are arranged and a center of the reception cell region Rr in which the four reception capacitive cells 18a to 18d are arranged are arranged adjacent to each other so that respective ultrasound transmission/reception directions in a radial scanning plane including directions A and B in FIG. 1 almost correspond to each other.

A rear end of the shaft 19 is connected to a rotation driving section 21 provided inside the operation portion 12. The rotation driving section 21 incorporates a motor therein, and drives rotation of the C-MUT 16 attached to the distal end of the hollow shaft 19 together with the hollow shaft 19.

The transmission ultrasound transducer 17 included in the C-MUT 16 makes ultrasound scan in a radial direction perpendicular to an axis of the insertion portion 11, and the reception ultrasound transducer 18 receives ultrasound retuned as a result of the ultrasound being reflected upon radial scanning.

The transmission ultrasound transducer 17 is connected to an end portion of a transmission signal cable 23a, which conveys an ultrasound transmission signal, via a transmission matching element 22, which serves as matching means (or a matching section) provided on the transducer mount 20. In the case of the configuration illustrated in, e.g., FIG. 2, first matching means or a first matching section for transmission signals is provided by the transmission matching element 22.

The transmission matching element 22 makes the end portion (output end) of the transmission signal cable 23a having a first characteristic impedance value Z1 match an electrical impedance (abbreviated simply as "impedance") of the transmission ultrasound transducer 17 to convey/apply an ultrasound transmission signal conveyed via the transmission signal cable 23a to the transmission ultrasound transducer 17 side. In other words, the transmission matching element 22 performs impedance matching for an ultrasound transmission signal conveyed via the transmission signal cable 23a to reduce occurrence of reflection and conveys the ultrasound transmission signal to the transmission ultrasound transducer 17 side.

The transmission signal cable 23a is inserted through a hollow portion of the shaft 19 and electrically connected via a slip ring 24 in the operation portion 12 to a transmission signal cable 23b (having the first characteristic impedance value Z1 that is the same as that of the transmission signal cable 23a) inserted in the ultrasound cable 13 outside the slip ring 24. Note that in FIG. 2, the transmission signal cables 23a and 23b are collectively indicated by a transmission signal cable 23.

Also, the reception ultrasound transducer 18 is connected to a reception signal cable 26a, via which ultrasound reception signals are conveyed, via a reception matching element 25, which serves as a matching means (or a matching section), provided on the transducer mount 20. In the case of the configuration illustrated in, e.g., FIG. 2, second matching means or a second matching section for reception signals is provided by the reception matching element 25.

The reception matching element 25 makes an impedance of the reception ultrasound transducer 18 that outputs an ultrasound reception signal match an end portion (entrance end) of the reception signal cable 26a having a second characteristic impedance value Z2 to convey the ultrasound reception signal outputted by the reception ultrasound transducer 18 to the reception signal cable 26a.

In other words, the reception matching element 25 performs impedance matching for the ultrasound reception signal outputted from the reception ultrasound transducer 18 to reduce occurrence of reflection and conveys the resulting ultrasound reception signal to the reception signal cable 26a side.

The reception signal cable 26a is inserted in the hollow portion of the shaft 19 and electrically connected via the slip ring 24 in the operation portion 12 to a reception signal cable 26b (having the second characteristic impedance value Z2, which is the same as that of the reception signal cable 26a) inserted in the ultrasound cable 13 outside the slip ring 24. Note that in FIG. 2, the reception signal cables 26a and 26b are collectively indicated by a reception signal cable 26.

Note that the first characteristic impedance value Z1 and the second characteristic impedance value Z2 may be equal to or different from each other.

The transmission signal cable 23b and the reception signal cable 26b are connected via the ultrasound connector 7 to a transmission circuit 31 and a reception circuit 32 provided inside the observation apparatus 3, through capacitors 33a and 33b, which serve as DC bias voltage blocking elements that block a DC bias voltage from being applied to the transmission circuit 31 and the reception circuit 32, and are also connected to a DC bias generation circuit 35 via a switch 34. In the present embodiment, a difference in impedance value between an output end from which the transmission circuit 31 outputs an ultrasound transmission signal and an end portion (input end) of the transmission signal cable 23b from which an ultrasound transmission signal is inputted is set to be small. Likewise, a difference in impedance value between an end portion (output end) of the reception signal cable 26b and an input end of the reception circuit 32 is set to be small. A case where such conditions as described above are not set will be described in a modification, which will be described later.

The observation apparatus 3 includes a control circuit 36 that controls operation of the transmission circuit 31, the reception circuit 32 and the DC bias generation circuit 35 and also controls switching operation for the switch 34.

The control circuit 36 performs switching control for the switch 34 as indicated by the solid line in ultrasound sending period or ultrasound transmission period (hereinafter simply "transmission period") in which ultrasound is sent out (transmitted).

The transmission circuit 31 generates a pulsed ultrasound transmission signal (under the control of the control circuit 36), and superimposes the transmission signal on a DC bias voltage generated by the DC bias generation circuit 35, and the resulting transmission signal is conveyed via the transmission signal cables 23b and 23a and applied to the four transmission capacitive cells 17a to 17d included in the transmission ultrasound transducer 17 via the transmission matching element 22.

FIG. 2 illustrates a schematic configuration of the four transmission capacitive cells 17a to 17d included in the transmission ultrasound transducer 17. In the transmission capacitive cells 17i (i=a, b, c, d), upper electrodes 37u and a lower electrode 37d are provided with a gap portion (vacuum space region) interposed therebetween. The lower electrode 37d is electrically connected in common to the four transmission capacitive cells 17a to 17d.

Although FIG. 2 illustrates the four transmission capacitive cells 17a to 17d formed in a belt-like region along a line extending a horizontal direction, as illustrated in FIG. 1, the four transmission capacitive cells 17a to 17d may be formed in a nearly square region of, i.e., two rows and two columns. Note that the shape of the transmission capacitive cell 17i is not limited to a shape such as a square shape and may be another shape such as a circular shape.

The ultrasound transmission signal superimposed on the DC bias voltage is applied to the four upper electrodes 37u via the transmission matching element 22, whereby respective upper films vibrate and generate ultrasound, and the transmission capacitive cells 17a to 17d send the ultrasound out. The sent-out ultrasound is made to exit toward the body cavity inner wall side from an outer peripheral face of the distal end portion 15 and reflected by a part in which the ultrasound impedance changes.

The control circuit 36 performs switching operation for the switch 34 as indicated by the dotted line in ultrasound reception period (hereinafter simply "reception period") in which ultrasound is received, and a DC bias voltage is applied to the four reception capacitive cells 18a to 18d included in the reception ultrasound transducer 18 to set the four reception capacitive cells 18a to 18d so as to receive ultrasound. The control circuit 36 sets the reception circuit 32 to be in an operating state.

As a result of repetition of the transmission periods and the reception periods (for example, from a first transmission period and a first reception period to an n-th transmission period and an n-th reception period), ultrasound data for generating an ultrasound tomographic image corresponding to radial scanning is obtained, and the ultrasound tomographic image is displayed on the first monitor 4.

As illustrated in FIG. 2, the reception capacitive cells 18i have a structure that is the same as that of the transmission capacitive cells 17i, members that are the same as those of the transmission capacitive cells 17i are provided with reference numerals that are the same as those of the transmission capacitive cells 17i and a description thereof will be omitted.

Incoming ultrasound as a result of reflection by the body cavity inner wall side is received by the four reception capacitive cells 18a to 18d included in the reception ultrasound transducer 18 arranged adjacent to the transmission ultrasound transducer 17, and the reception capacitive cells 18a to 18d generate ultrasound reception signals.

The generated ultrasound reception signals are conveyed to the reception signal cable 26 via the reception matching element 25 and inputted to the reception circuit 32 from the output end of the reception signal cable 26. The reception circuit 32 generates an ultrasound tomographic image corresponding to a mechanical radial scan, and outputs the ultrasound tomographic image to the first monitor 4. On a display surface of the first monitor 4, the ultrasound tomographic image is displayed as an ultrasound image.

At a position on the proximal end side of the distal end portion 15 of the ultrasound endoscope 2, a light-emitting diode (abbreviated as "LED") 41, which serves as an illumination element that performs illumination, an objective lens 42, and an image pickup device 43 arranged at a position where an image through the objective lens 42 is formed are provided.

The LED 41 is connected to an LED power supply circuit 45 in the endoscope processor 5 via a power supply wire 44 inserted in the insertion portion 11 and the endoscope cable 14. The LED power supply circuit 45 supplies LED power for making the LED 41 emit light to the LED 41.

The objective lens 42 forms an optical image of an object such as a diseased part illuminated by the LED 41 on an image-pickup surface of the image pickup device 43. The image pickup device 43 photoelectrically converts the optical image on the image-pickup surface and outputs the resulting signal to the signal processing circuit 47 in the endoscope processor 5 via a signal wire 46 inserted in the insertion portion 11 and the endoscope cable 14. The signal processing circuit 47 performs signal processing for generating an endoscopic image corresponding to the optical image formed on the image pickup surface, and outputs the endoscopic image to the second monitor 6, and the endoscopic image is displayed on a display surface of the second monitor 6.

Note that, although the present embodiment has been described in terms of an example configuration of the ultrasound endoscope 2 having an endoscope function in addition to an ultrasound probe, which is an ultrasound probe including a C-MUT, a configuration with no endoscope function may be employed.

FIG. 3 illustrates an example configuration of the transmission matching element 22 and the reception matching element 25 in the present embodiment. The transmission matching element 22 and the reception matching element 25 are each provided using coils and a capacitor.

An outer conductor at an end portion of a coaxial cable included in the transmission signal cable 23*a* is connected to the lower electrode 37*d* of the transmission ultrasound transducer 17, and a center conductor at the end portion of the coaxial cable is connected to the upper electrodes 37*u* of the (parallelly-connected) four transmission capacitive cells 17*a* to 17*d* in the transmission ultrasound transducer 17 via two coils 51 and 52 connected in series, and a point of connection between the two coils 51 and 52 is connected to the (common) lower electrode 37*d* via a capacitor 53.

The transmission ultrasound transducer 17 is configured using the coils 51 and 52 and the capacitor 53 to achieve impedance matching between, mainly, capacitance components of the parallelly-connected four transmission capacitive cells 17*a* to 17*d* and, mainly, an inductance component of the coaxial cable included in the transmission signal cable 23*a*.

Also, the lower electrode 37*d* of the reception ultrasound transducer 18 is connected to an outer conductor at an end portion of a coaxial cable included in the reception signal cable 26*a*, the (parallelly-connected) four upper electrodes 37*u* in the transmission ultrasound transducer 17 are connected to a center conductor at the end portion of the coaxial cable via serially connected two coils 54 and 55, and a point of connection between the two coils 54 and 55 is connected to the lower electrode 37*d* via a capacitor 56.

The reception ultrasound transducer 18 is configured using the coils 54 and 55 and the capacitor 56 to achieve an impedance match between, mainly, capacitive components of the parallelly-connected four reception capacitive cells 18*a* to 18*d* and, mainly, an inductance component of the coaxial cable included in the reception signal cable 26*a*.

Note that, although the present embodiment has been described in terms of an example in which the coils and the capacitor included in respective matching means (or respective matching sections) are arranged in the vicinity of the transmission ultrasound transducer 17 or the reception ultrasound transducer 18, a more proper arrangement may be employed according to the characteristics of the transmission capacitive cells 17*a* to 17*d* included in the transmission ultrasound transducer 17 or the characteristics of the reception capacitive cells 18*a* to 18*d* included in the reception ultrasound transducer 18, and the characteristics of the coaxial cable included in the transmission signal cable 23*a* or the reception signal cable 26*a*. The same applies also to a case where the configuration of the matching means (or the matching section) has been changed as described below.

Although FIG. 3 indicates an example in which the transmission matching element 22 and the reception matching element 25, which each serve as matching means (or a matching section), are configured using coils and a capacitor, the configuration of the transmission matching element 22 and the reception matching element 25 is not limited to the configuration illustrated in FIG. 3. For example, in FIG. 3, a configuration in which only a capacitor is connected in parallel to the upper electrodes 37*u* and the lower electrode 37*d* of the transmission ultrasound transducer 17 or the reception ultrasound transducer 18 without using coils and the center conductor and the outer conductor of the coaxial cable are connected to opposite ends of the capacitor may be employed.

Also, for the matching means (or the matching section), a transformer that transforms an impedance may be used.

The ultrasound diagnostic apparatus 1 configured as described above includes: an ultrasound endoscope 2, which serves as an ultrasound probe including a capacitive micromachined ultrasound transducer (C-MUT 16); an observation apparatus 3, which serves as an ultrasound observation apparatus to which the ultrasound probe is detachably connected, the ultrasound observation apparatus including the transmission circuit 31 that generates an ultrasound transmission signal for sending ultrasound out from the capacitive micromachined ultrasound transducer and a reception circuit 32 that performs signal processing on an ultrasound reception signal generated as a result of ultrasound being received by the capacitive ultrasound micromachined transducer; the transmission ultrasound transducer 17 and the reception ultrasound transducer 18 included in the capacitive ultrasound micromachined transducer, the transmission ultrasound transducer 17 including the plurality of transmission capacitive cells 17*a* to 17*d* that each send ultrasound out, the reception ultrasound transducer 18 including the plurality of reception capacitive cells 18*a* to 18*d* that each receive reflected ultrasound of the sent-out ultrasound and output an ultrasound reception signal; the transmission signal cables 23*a* and 23*b* connecting the transmission ultrasound transducer 17 and the transmission circuit 31 in the ultrasound observation apparatus; the reception signal cables 26*a* and 26*b* connecting the reception ultrasound transducer 18 and the reception circuit 32 in the ultrasound observation apparatus; the transmission matching element 22 and the reception matching element 25, which serve as a first matching section and a second matching section that perform electrical impedance matching for the ultrasound transmission signal conveyed by the transmission signal cables 23*a* and 23*b* and the ultrasound reception signal conveyed by the reception signal cables 26*a* and 26*b*, respectively.

Next, an operation of the present embodiment will be described.

As illustrated in FIG. 1, the ultrasound endoscope 2 is connected to the observation apparatus 3 and the endoscope processor 5, and the insertion portion 11 is inserted into a body cavity of a patient to start an ultrasound examination of a part such as a diseased part while an endoscopic image provided by the image pickup device 43 is observed.

In a first transmission period, the control circuit 36 controls operation of the rotation driving section 21 and also controls operation of the transmission circuit 31, the reception circuit 32, the switch 34 and the DC bias generation circuit 35.

The transmission circuit 31 generates a pulsed ultrasound transmission signal, the ultrasound transmission signal is superimposed on a DC bias voltage generated in the DC bias generation circuit 35, and the transmission signal cables 23b and 23a convey the ultrasound transmission signal superimposed on the DC bias voltage to the respective distal ends.

The ultrasound transmission signal superimposed on the DC bias voltage passes through the transmission matching element 22 and is applied to the transmission capacitive cells 17a to 17d included in the transmission ultrasound transducer 17.

In this case, impedance matching between the end portion of the transmission signal cable 23a and the parallelly-connected transmission capacitive cells 17a to 17d included in the transmission ultrasound transducer 17 is performed by the transmission matching element 22.

Therefore, the ultrasound transmission signal, which is in a nearly ideal state, is applied to the (parallelly-connected) four transmission capacitive cells 17a to 17d without the ultrasound transmission signal being reflected because of an impedance mismatch, or signal waveform distortion caused as a result of the reflected ultrasound transmission signal being superimposed on the original ultrasound transmission signal. Thus, a decrease in S/N ratio due to signal waveform distortion and occurrence of a decrease in signal level due to reflection of the ultrasound transmission signal can be reduced (or suppressed).

The four transmission capacitive cells 17a to 17d generate respective ultrasound and send the generated ultrasound out from the respective upper film sides. An intensity of the sent-out ultrasound can be increased by driving the plurality of (four in the specific example) transmission capacitive cells 17a to 17d.

The sent-out ultrasound advances to the inside of an inner wall (deep part of the inner wall) of, e.g., a diseased part in the body cavity and is reflected by a part where the ultrasound impedance (acoustic impedance) changes, and returns to the transmission capacitive cells 17a to 17d side as reflected ultrasound. Note that in a first reception period after the generation of the pulsed ultrasound transmission signal, the control circuit 36 switches the switch 34 to apply the DC bias voltage to the reception signal cables 26b and 26a. Then, the control circuit 36 sets the reception circuit 32 to be in an operating state.

The reception capacitive cells 18a to 18d included in the reception ultrasound transducer 18 are arranged adjacent to the transmission capacitive cells 17a to 17d. Accordingly, the reflected ultrasound that has returned is received by the reception capacitive cells 18a to 18d included in the reception ultrasound transducer 18 and converted into ultrasound reception signals and outputted from the reception capacitive cells 18a to 18d.

The ultrasound reception signals outputted from the reception capacitive cells 18a to 18d are inputted to the end portion of the reception signal cable 26a through the reception matching element 25.

In this case, the impedances of the reception capacitive cells 18a to 18d and the impedance of the end portion of the reception signal cable 26a are matched by the reception matching element 25, and thus, the ultrasound reception signals are conveyed to the reception signal cable 26a side without signal waveform distortion due to an impedance mismatch. Thus, a decrease in S/N ratio and receiving sensitivity due to signal waveform distortion can be prevented.

The ultrasound reception signals conveyed to the reception signal cable 26a are inputted to the reception circuit 32 via the reception signal cable 26b.

The reception circuit 32 performs image processing on the inputted ultrasound signals and stores the resulting image in a memory as first sound-ray data. Upon an end of the first reception period, a second transmission period starts and the switch 34 is switched.

Since the C-MUT 16 is rotated by the rotation driving section 21, a direction in which ultrasound is transmitted/received by the C-MUT 16 is slightly different from that in the first transmission period. The operation in the second transmission period is the same as that in the first transmission period except the difference in ultrasound transmission direction.

Subsequent to the second transmission period, a second reception period starts, and in this case, also, the operation is the same as that in the first reception period except a difference in ultrasound reception direction. Accordingly, in this case, second sound-ray data is stored in the memory.

Consequently, an operation similar to the above is repeated until the n-th transmission period and the n-th reception period, an ultrasound tomographic image as an ultrasound image is generated from n pieces of sound-ray data corresponding to radial scanning and outputted to the first monitor 4. On the display surface of the first monitor 4, an ultrasound tomographic image with reflection of the ultrasound transmission signals and the ultrasound reception signals reduced and signal waveform distortion reduced and thus with a high receiving sensitivity and a good S/N ratio is displayed.

As described above, the present embodiment includes matching means (or a matching section) that performs electrical impedance matching for each of an ultrasound transmission signal at the time of ultrasound transmission and an ultrasound reception signal at the time of ultrasound reception. Also, for ultrasound transmission and ultrasound reception, the dedicated transmission ultrasound transducer 17 and the dedicated reception ultrasound transducer 18 are provided, respectively.

Accordingly, the present embodiment enables prevention of occurrence of, e.g., a decrease in receiving sensitivity due to an impedance mismatch at the time of any of ultrasound transmission and ultrasound reception, and thus enables obtainment of an ultrasound image with a good receiving sensitivity and a good S/N ratio. For a more detailed description, the present embodiment enables reduction in signal waveform distortion due to ultrasound transmission signal reflection caused by an impedance mismatch, prevention of a decrease in intensity of ultrasound due to reflection and reduction in signal waveform distortion due to reflection caused by an impedance mismatch when an ultrasound reception signal generated by the reception ultrasound transducer 18 is conveyed to the reception circuit 32 via the reception signal cables 26a and 26b, as well as prevention of a decrease in intensity of the signal and thus obtainment of an ultrasound image with a good S/N ratio. Furthermore, the present embodiment enables obtainment of an ultrasound image with a good S/N ratio, and thus, makes a surgeon that performs diagnosis by observing an ultrasound image easily perform proper diagnosis.

Since the transmission ultrasound transducer 17 and the reception ultrasound transducer 18, which are dedicated to ultrasound transmission and ultrasound reception, respectively, are used, ultrasound transmission and ultrasound reception with more proper characteristics can be performed and impedance matching can also be performed more properly, compared to a case where a transducer that performs both transmission and reception is used. Thus, the present embodiment enables ultrasound transmission and ultrasound reception to be performed in a nearly ideal state compared to the related art.

Figure 4:
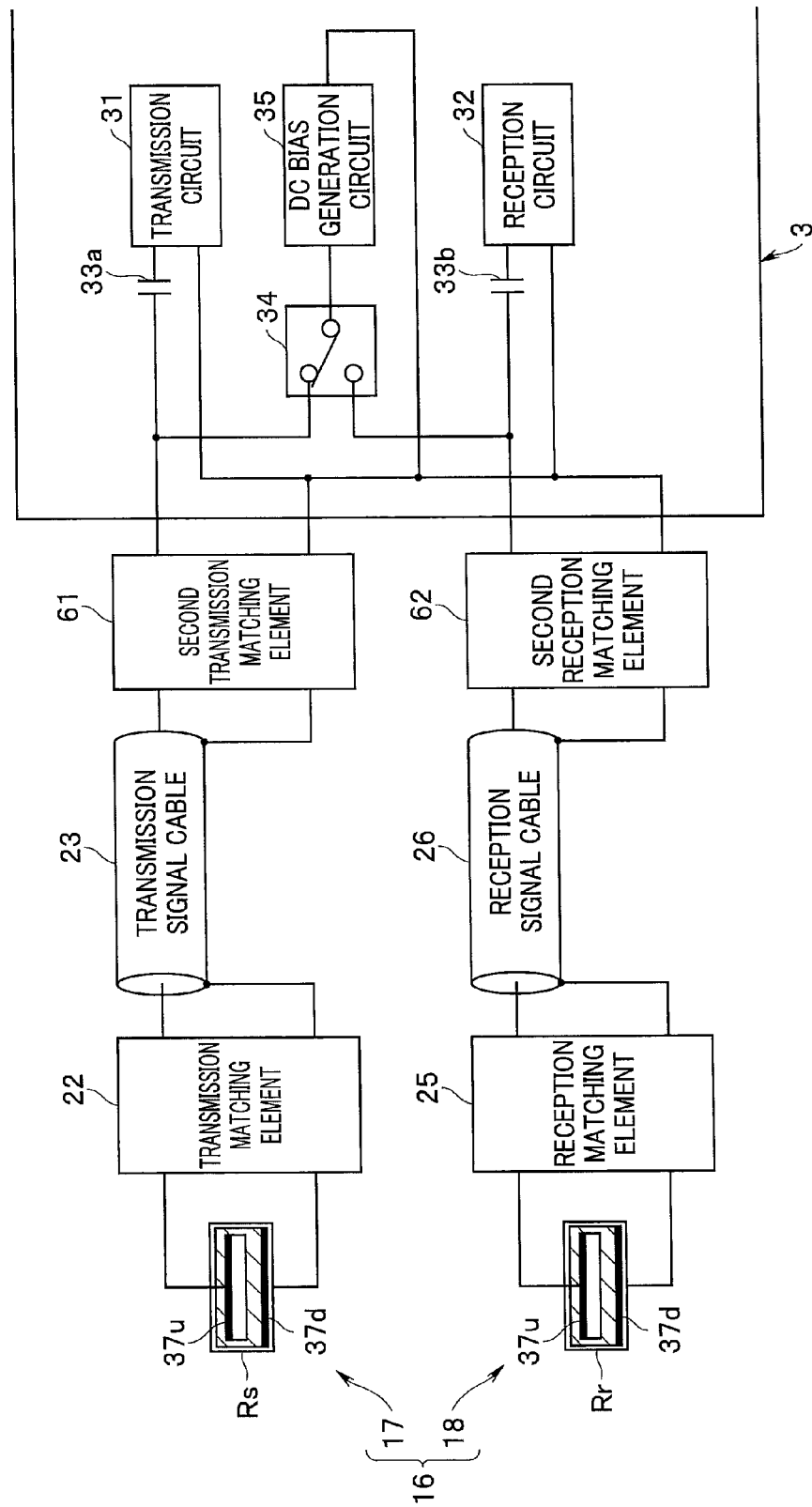
FIG. 4 is a block diagram illustrating a configuration of a circuit system that transmits/receives ultrasound in a modification of the first embodiment.

FIG. 4 illustrates a configuration of a circuit system that transmits and receives ultrasound according to a modification of the present embodiment. The above first embodiment has been described in terms of a case where the difference in impedance value between the output end of the transmission circuit 31 and the input end of the transmission signal cable 23b is small and the difference in impedance value between the output end of the reception signal cable 26b and the input end of the reception circuit 32 is small.

If these impedance value differences are not small, as illustrated in FIG. 4, a configuration in which a second transmission signal matching element 61 is arranged between an output end of a transmission circuit 31 and an input end of a transmission signal cable 23b, a second reception signal matching element 62 is arranged between an output end of a reception signal cable 26b and an input end of a reception circuit 32 may be employed. In this case, the second transmission signal matching element 61 and the second reception signal matching element 62 may be provided, for example, inside the ultrasound connector 7 illustrated in FIG. 1. In the case of the configuration illustrated in FIG. 4, first matching means or a first matching section for transmission signals includes a transmission signal matching element 22 and the second transmission signal matching element 61, and second matching means or a second matching section for reception signals includes a reception signal matching element 25 and the second reception signal matching element 62.

Note that in FIG. 4, the plurality of transmission capacitive cells 17a to 17d and the plurality of reception capacitive cells 18a to 18d illustrated in, e.g., FIG. 2 are indicated in a simplified manner by one transmission ultrasound transducer 17 and one reception ultrasound transducer 18. Also, in FIG. 4, illustration of a control circuit 36 is omitted.

The second transmission signal matching element 61 and the second reception signal matching element 62 may be configured using a transmission matching element 22 and a reception matching element 25, such as illustrated in FIG. 3, each using coils and a capacitor, may be configured using capacitors, or may be configured using other known elements.

As illustrated in FIG. 4, further provision of the second transmission signal matching element 61 and the second reception signal matching element 62 enables reduction in, e.g., signal waveform distortion (due to an impedance mismatch) where an ultrasound transmission signal is conveyed (outputted) from the transmission circuit 31 to the transmission signal cable 23 side and reduction in, e.g., signal waveform distortion (due to impedance matching) where an ultrasound reception signal is inputted from the reception signal cable 26 to the reception circuit 32.

Accordingly, an ultrasound image with a further enhanced receiving sensitivity and S/N ratio in addition to the effects of the first embodiment can be obtained.

(Second Embodiment)

Figure 5:
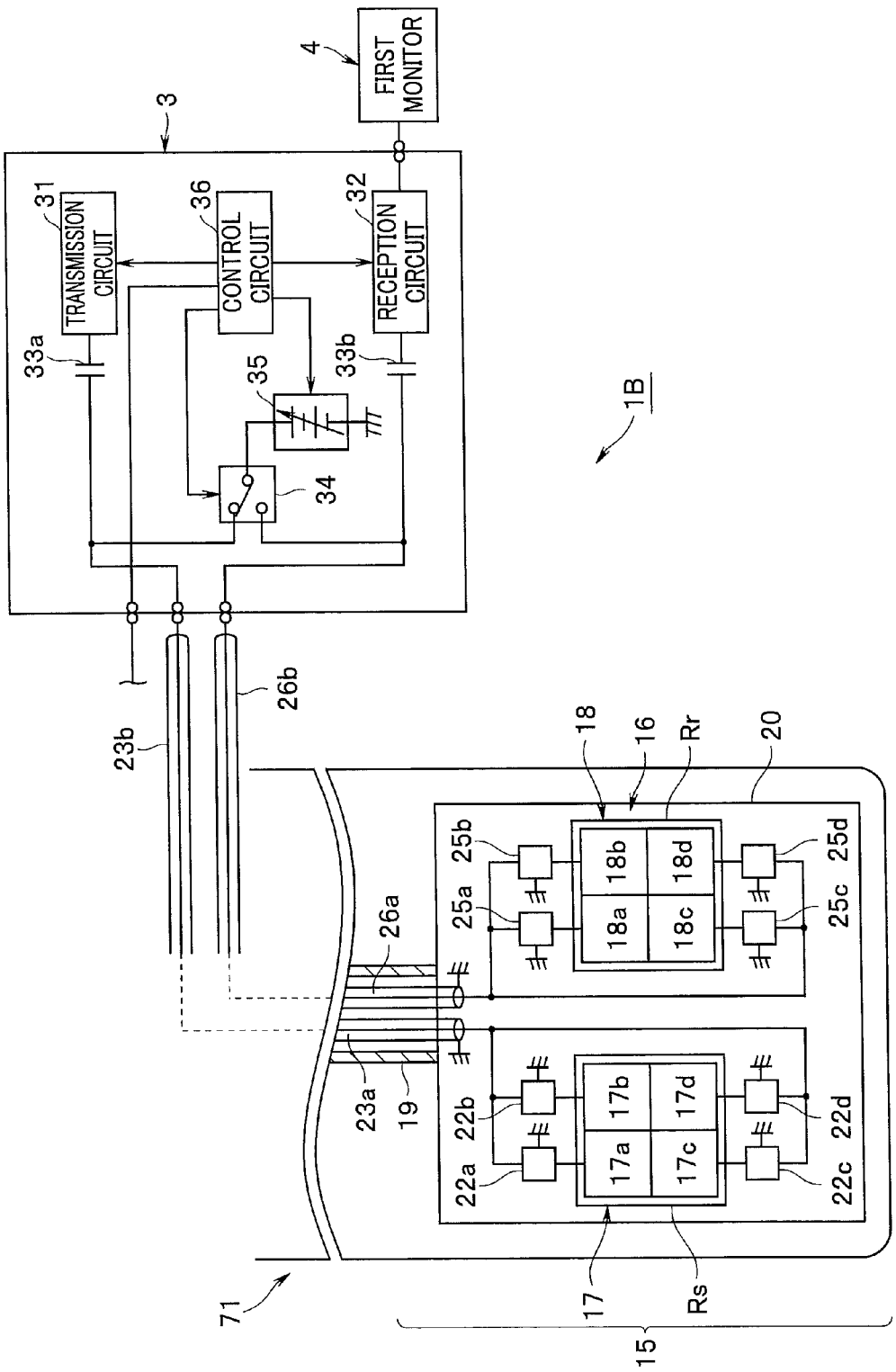
FIG. 5 is a diagram illustrating a schematic configuration of an ultrasound diagnostic apparatus according to a second embodiment of the present invention.

FIG. 5 illustrates a schematic configuration of an ultrasound diagnostic apparatus 1B according to a second embodiment of the present invention. The ultrasound diagnostic apparatus 1B includes an ultrasound probe 71, an observation apparatus 3 and a first monitor 4.

Although in FIG. 1, the ultrasound endoscope 2 is provided, in the present embodiment, the ultrasound probe 71 is used instead of the ultrasound endoscope 2. The ultrasound probe 71 has a structure without the endoscope function (the LED 41, the objective lens 42 and the image pickup device 43) in the ultrasound endoscope 2 in FIG. 1. Note that in FIG. 5, illustration of, e.g., a rotation driving section 21 is omitted.

In the first embodiment described above, impedance matching is performed in common for the four transmission capacitive cells 17a to 17d in the transmission cell region Rs by one transmission matching element 22 and impedance matching is performed in common for the reception capacitive cells 18a to 18d in the reception cell region Rr by one reception matching element 25.

On the other hand, in the present embodiment, impedance matching is performed in units of transmission capacitive cells 17i (that is, for respective transmission capacitive cells 17i) in a transmission cell region Rs by respective transmission matching elements 22i, and impedance matching is performed in units of reception capacitive cells 18i in a reception cell region Rr by respective reception matching elements 25i.

For example, a transmission capacitive cell 17a (an upper electrode 37u and a lower electrode 37d of the transmission capacitive cell 17a) in the transmission cell region Rs, for which impedance matching is performed by a transmission matching element 22a provided in the vicinity of or near the transmission capacitive cell 17a, is connected to a center conductor and an outer conductor at an end portion of a coaxial cable included in a transmission signal cable 23a. The same applies to the other transmission capacitive cells 17b-17d.

Also, for example, a reception capacitive cell 18a (an upper electrode 37u and a lower electrode 37d of the reception capacitive cell 18a) in the reception cell region Rr, for which impedance matching is performed by a reception matching element 25a arranged near the reception capacitive cell 18a, is connected to a center conductor and an outer conductor at an end portion of a coaxial cable included in a reception signal cable 26a. The same applies to the other reception capacitive cells 18b-18d.

Note that the transmission matching elements 22i and the reception matching elements 25i may be each configured using, for example, the coils and the capacitor illustrated in FIG. 3, may be configured using capacitors, or may be configured using other known elements.

The configuration of the observation apparatus 3 has been described with reference to FIG. 1 and a description thereof will be omitted.

According to the present embodiment, even if the plurality of (four in the specific example) transmission capacitive cells 17a to 17d in the transmission cell region Rs vary in characteristic (for example, impedance value), impedance matching between the transmission signal cable 23a and the transmission capacitive cells 17a to 17d can be performed by the transmission matching elements 22i according to the respective characteristics of the transmission capacitive cells 17i.

Also, according to the present embodiment, even if the plurality of (four in the specific example) the reception capacitive cells 18a to 18d in the reception cell region Rr vary in characteristic (for example, impedance value), impedance matching between the reception signal cable 26a and the reception capacitive cells 18a to 18d can be performed by the reception matching elements 25i according to the respective characteristics of the reception capacitive cells 18i.

Accordingly, the effect of providing a further enhanced receiving sensitivity and S/N ratio can be provided in addition to effects similar to those of the first embodiment. Note that in the present embodiment, also, the second transmission matching element 61 and the second reception matching element 62 illustrated in FIG. 4 may be provided.

(Third Embodiment)

Figure 6:
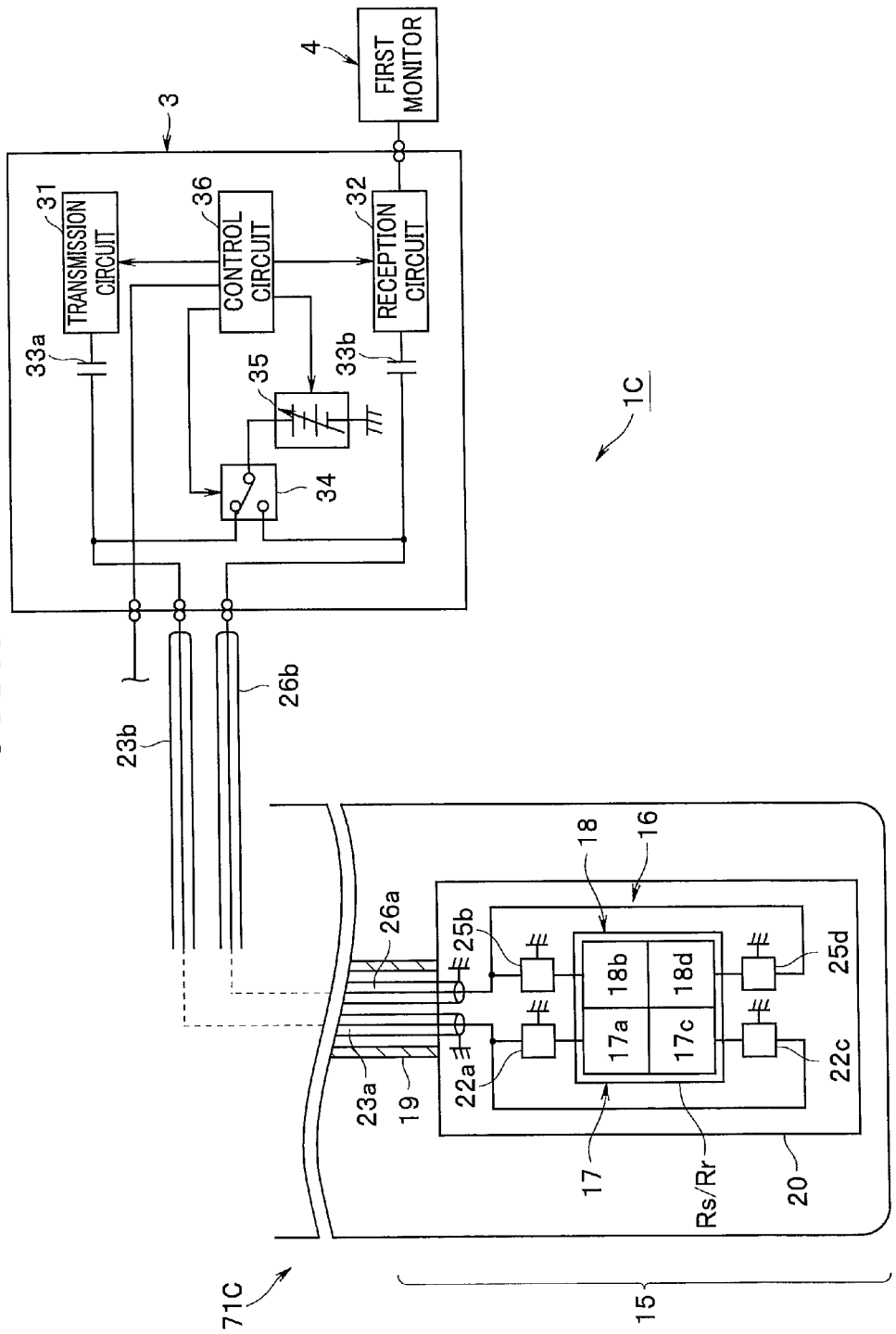
FIG. 6 is a diagram illustrating a schematic configuration of an ultrasound diagnostic apparatus according to a third embodiment of the present invention.

FIG. 6 illustrates a schematic configuration of an ultrasound diagnostic apparatus 1C according to a third embodiment of the present invention. The ultrasound diagnostic apparatus 1C includes an ultrasound probe 71C, an observation apparatus 3 and a first monitor 4.

Although in the ultrasound diagnostic apparatus 1B illustrated in FIG. 5, the transmission cell region Rs and the reception cell region Rr are formed adjacent to each other, in the present embodiment, the ultrasound probe 71C is formed in such a manner that transmission capacitive cells 17a and 17c and reception capacitive cells 18b and 18d are mixed in a transmission/reception cell region Rs/Rr, which has a same size as that of the transmission cell region Rs or the reception cell region Rr in the ultrasound probe 71 illustrated in FIG. 5.

Impedance matching between the transmission capacitive cells 17a and 17c and a transmission signal cable 23a is performed by transmission matching elements 22a and 22c, respectively, and impedance matching between the reception capacitive cells 18b and 18d and a reception signal cable 26a is performed by reception matching elements 25b and 25d, respectively.

The rest of the configuration is similar to the configuration illustrated in FIG. 5.

According to the present embodiment, a transmission region from which ultrasound is transmitted in order to generate information for one pixel in an ultrasound image and a reception region in which ultrasound is received in order to obtain information for one pixel are provided in a common region, enabling obtainment of an ultrasound image with high resolution.

Also, as in the case of the second embodiment, even if the transmission capacitive cells 17a and 17c and the reception capacitive cells 18b and 18d in the transmission/reception cell region Rs/Rr vary in impedance value, impedance matching can be performed according to the respective characteristics of the transmission capacitive cells 17a and 17c and the reception capacitive cells 18b and 18d. Thus, an ultrasound image with a good receiving sensitivity and a good S/N ratio can be obtained.

Note that also in the present embodiment, the second transmission matching element 61 and the second reception matching element 62 illustrated in FIG. 4 may be provided.

Although the above embodiment has been described in terms of an ultrasound diagnostic apparatus that makes a C-MUT 16 perform mechanical scanning, the present invention can be applied to an ultrasound diagnostic apparatus that makes a C-MUT perform electronic scanning.

Figure 7:
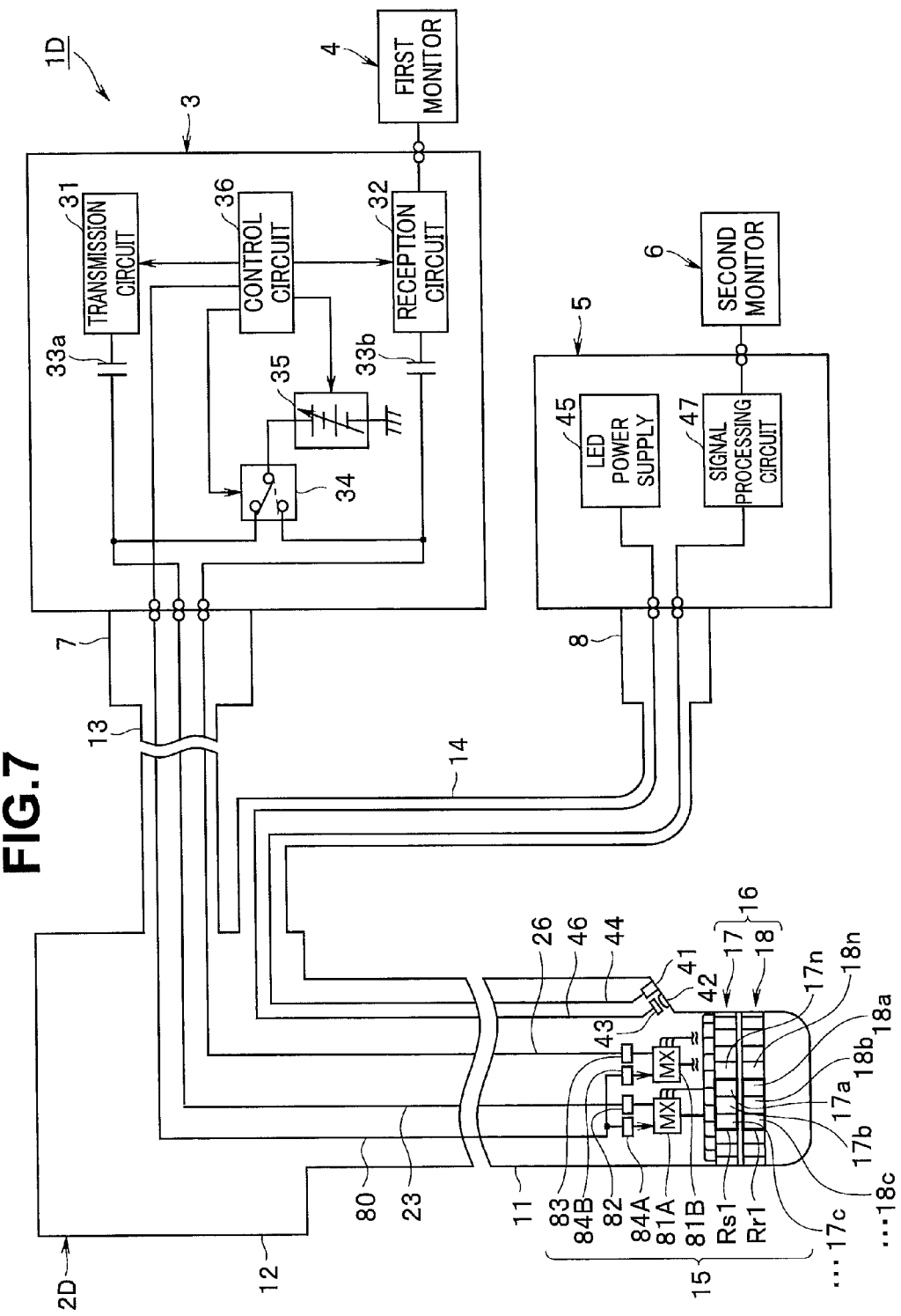
FIG. 7 is a configuration of an electronic scanning-type ultrasound diagnostic apparatus in the present invention.

FIG. 7 illustrates a configuration of an ultrasound diagnostic apparatus 1D according to a second modification of the first embodiment, which makes a C-MUT 16 perform electronic scanning instead of the ultrasound diagnostic apparatus 1 that makes the C-MUT 16 perform mechanical scanning in FIG. 1. The ultrasound diagnostic apparatus 1D includes an endoscope 2D instead of the endoscope 2 in the ultrasound diagnostic apparatus 1 in FIG. 1. In the endoscope 2D, a transmission ultrasound transducer 17 and a reception ultrasound transducer 18 included in a C-MUT 16 are provided adjacent to each other along an outer circumferential face of a distal end portion 15. The transmission ultrasound transducer 17 and the reception ultrasound transducer 18 include an ultrasound transducer array in which n transmission capacitive cells 17a to 17n and n reception capacitive cells 18a to 18n are arranged along respective (circular) lines. Note that annular regions in which the transmission capacitive cells 17a to 17n and the reception capacitive cells 18a to 18n are arranged, respectively, provide a transmission cell region and a reception cell region corresponding to an entire ultrasound scanning region. In the present modification, as described later, a transmission cell region Rs1 and a reception cell region Rr1 move (shift) according to the ultrasound scanning direction that changes temporally. Thus, along with movement of the transmission cell region Rs1 and the reception cell region Rr1, transmission capacitive cells 17k and reception capacitive cells 18k move.

Transmission capacitive cells 17j (j=a, b, c, . . . n) are connected n terminals of a first multiplexer 81A arranged in, for example, the distal end portion 15, and a decoder 84A, to which clocks (mode signal), which are selection control signals (synchronized with the above-described transmission periods) conveyed via a cable 80 from a control circuit 36, are applied, is provided in the vicinity of the first multiplexer 81A. The decoder 84A generates selection signals from a clock applied (inputted) thereto and outputs the generated selection signals to the first multiplexer 81A, and the first multiplexer 81A sequentially selects a plurality of (for example, three) transmission capacitive cells based on the selection signals. An ultrasound transmission signal with a DC bias voltage superimposed thereon is applied from a transmission circuit 31 to the selected three transmission capacitive cells 17k (k=a, b, c; b, c, d; c, d, e; . . . ) via a transmission signal cable 23. As described above, upon an input of a selection control signal, the decoder 84A generates selection signals for selecting a plurality of (three in the specific example) transmission capacitive cells 17k used for ultrasound transmission, for the first multiplexer 81A.

The transmission signal cable 23 conveys an ultrasound transmission signal and a DC bias voltage from an observation apparatus 3 to which an ultrasound connector 7 is connected, to apply the ultrasound transmission signal and the DC bias voltage to three transmission capacitive cells 17k selected by the first multiplexer 81A through a transmission matching element 82, which provides matching means (or a matching section), arranged in the vicinity of the first multiplexer 81A and the transmission ultrasound transducer 17 in the distal end portion 15.

Figure 8:
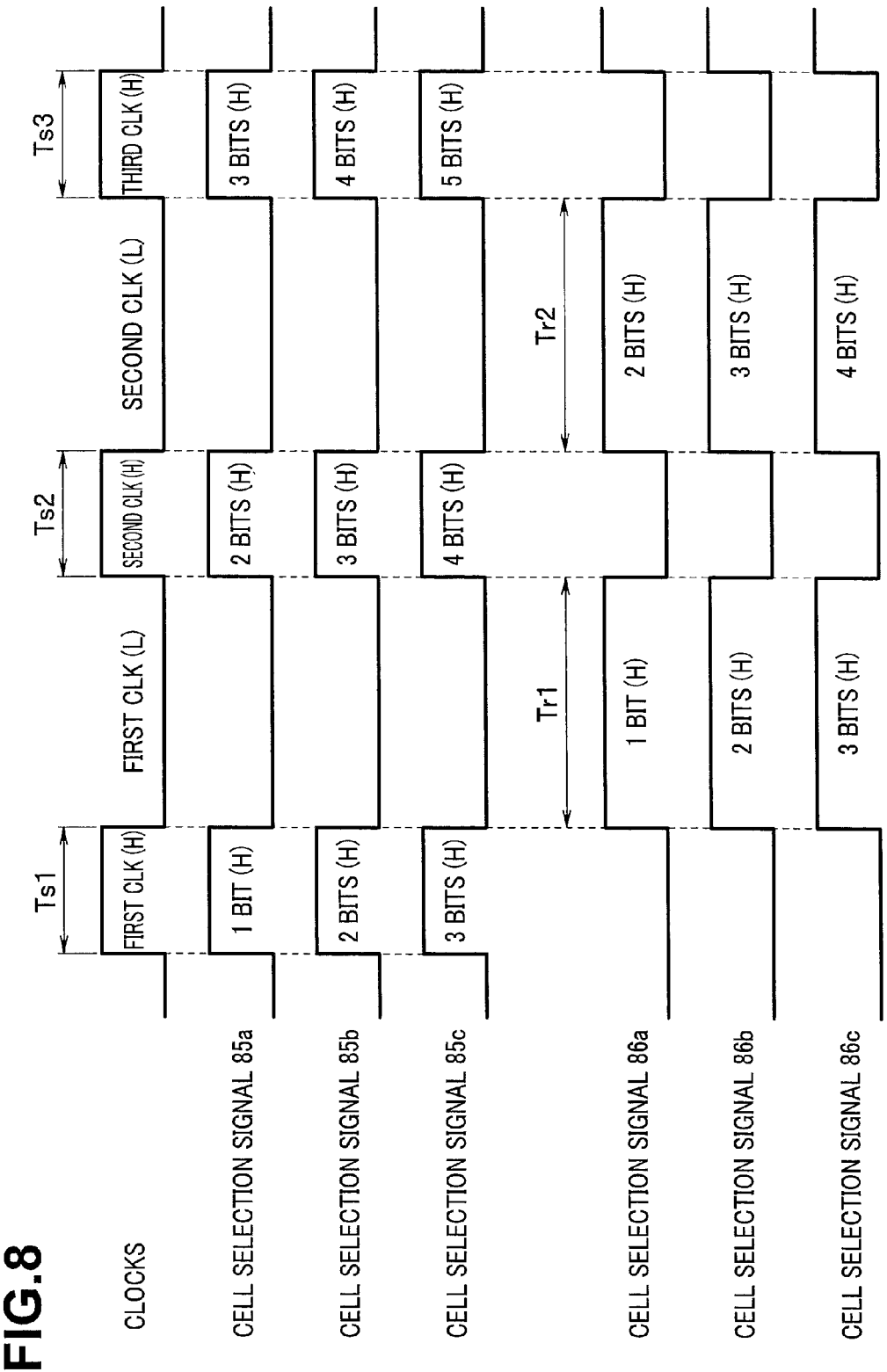
FIG. 8 is a diagram indicating timings of, e.g., selection signals generated from a selection control signal.

Note that the first multiplexer 81A sequentially selects three transmission capacitive cells 17k according to the alignment order in such a manner that the first multiplexer 81A selects the transmission capacitive cells 17a, 17b and 17c in a period in which a first clock of the selection control signal, the first clock being synchronized with a first transmission period, is at an H level, based on selection signals from the decoder 84A, selects the transmission capacitive cells 17b, 17c and 17d in a period in which a second clock is at an H level, and selects the transmission capacitive cells 17c, 17d and 17e in a period in which a third clock is at an H level. FIG. 8 is a timing chart for description of operation of clocks, which serve as a selection control signal applied (inputted) to the decoder 84A, and selection signals outputted from the decoder 84A. First, second, . . . clocks (abbreviated as the first CLK, the second CLK, . . . ), which serve as a selection control signal, are outputted in synchronization with first, second, ... transmission periods (Ts1, Ts2, ... ). The decoder 84A generates three cell selection signals 85a, 85b and 85c, which serve as selection signals, from such clocks and outputs the cell selection signals 85a, 85b and 85c to three selection control terminals that control selection made by the first multiplexer 81A. Note that the decoder 84A (as well as the later-described decoder 84B) is configured using, e.g., a ring counter that counts clocks and an adder circuit that adds up the clocks, which are not illustrated. In FIG. 8, clocks, which serve as a selection control signal whose H level and L level periods are synchronized with transmission periods and reception periods, respectively, are generated by not-illustrated reference clocks.

Upon an input of a first clock, which serves as a selection control signal synchronized with a first transmission period Ts1, which is a first transmission period, the decoder 84A counts a rising edge of the first clock, and outputs a cell selection signal 85a with only one H level bit as an output value (count value) from a first output end, outputs a cell selection signal 85b with two H level bits (one bit added to one bit from the first output end) as an output value from a second output end, and outputs a cell selection signal 85c with three H level bits (one bit added to two bits from the second output end) as an output value from a third output end, to the selection control terminals of the first multiplexer 81A. The first multiplexer 81A is set so as to select three transmission capacitive cells 17k according to the bit counts, which are the output values of the cell selection signals 85a, 85b and 85c outputted by the decoder 84A. The first multiplexer 81A is set so as to select, for example, if a bit count Ba of the cell selection signal 85a (or 85b or 85c) is Ba=1 bit, select the transmission capacitive cell 17a, if Ba=2 bits, select the transmission capacitive cell 17b, ..., and if Ba=n bits, select the transmission capacitive cell 17n, respectively. The reference numeral n indicates the number of transmission capacitive cells as described above.

Also, the first multiplexer 81A is configured so as to, if the bit count Ba reaches Ba=n, the decoder 84A resets the bit count Ba to zero immediately before an input of a next (n+1)-th clock, and upon an input of the (n+1)-th clock, output a one-bit cell selection signal 85a. Accordingly, if the bit counts of the cell selection signals 85a, 85b and 85c are one bit, two bits and three bits, respectively, the first multiplexer 81A selects the transmission capacitive cells 17a, 17b and 17c, which is a first, a second and a third in the alignment order.

Also, upon an input of a second clock as a selection control signal synchronized with a second transmission period Ts2, the decoder 84A outputs a cell selection signal 85a with two H level bits (one bit added to the previous one bit) as an output value from the first output end, outputs a cell selection signal 85b with three H level bits (one bit added to two bits from the first output end) as an output value from the second output end, and outputs a cell selection signal 85c with four H level bits (one bit added to three bits from the second output end) as an output value from the third output end, to the first multiplexer 81A. Accordingly, in this case, the first multiplexer 81A selects the transmission capacitive cells 17b, 17c and 17d in the second, the third and a fourth in the alignment order. As described above, three transmission capacitive cells 17k are sequentially selected according to the alignment order. Then, the selected three transmission capacitive cells 17k radially transmit ultrasound to make the ultrasound (beams) scan radially. In the present modification, the transmission cell region Rs1 for forming ultrasound beams for one pixel includes three transmission capacitive cells 17k, and the transmission cell region Rs1 moves according to a direction (or a narrow radial region) in which ultrasound is transmitted, in the transmission ultrasound transducer 17 (that is, the n transmission capacitive cells 17a to 17n) included in a transmission region for a case where ultrasound is made to radially scan. However, the predetermined transmission cell region Rs1 is determined according to the direction (or the narrow radial region) in which ultrasound is transmitted. On the other hand, in the first embodiment, the transmission cell region Rs remains unchanged even if the ultrasound transmission direction changes.

The transmission matching element 82 makes an end portion (output end) of a transmission signal cable 23 having, for example, a first characteristic impedance value Z1 match impedances of three parallelly-connected transmission capacitive cells 17k used for ultrasound transmission to convey (apply) an ultrasound transmission signal conveyed from the transmission signal cable 23, to the transmission capacitive cells 17k. In other words, the transmission matching element 82 performs impedance matching for the ultrasound transmission signal conveyed from the transmission signal cable 23 to reduce occurrence of reflection and applies the resulting ultrasound transmission signal to the three transmission capacitive cells 17k included in the transmission ultrasound transducer 17. Note that, although in the example illustrated in FIG. 7, impedance matching for the selected three parallel-connected transmission capacitive cells 17k is performed by one transmission matching element 82, impedance matching may be performed for each one selected transmission capacitive cell 17k. Also, if impedance matching is performed for each one transmission capacitive cell 17k, as illustrated in FIG. 9, the transmission signal cable 23 may include three coaxial cables.

Figure 9:
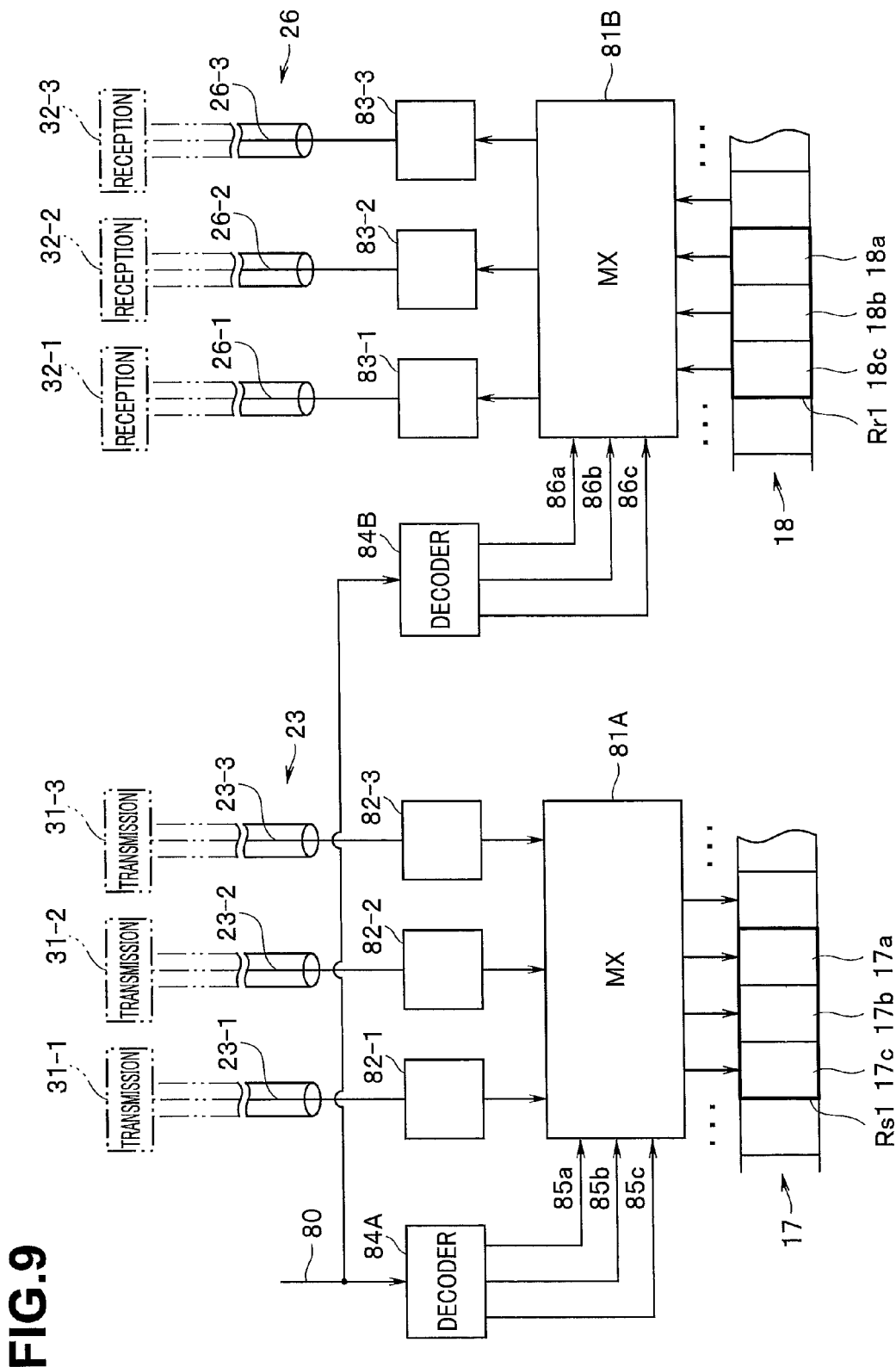
FIG. 9 is a diagram illustrating a configuration of a transmission ultrasound transducer peripheral portion and a reception ultrasound transducer peripheral portion that are configured so that impedance matching is performed for each of transmission and reception capacitive cells used for ultrasound transmission/reception.

As illustrated in FIG. 9, end portions of three coaxial cables 23-1, 23-2 and 23-3 included in the transmission signal cable 23 are connected to respective transmission capacitive cells 17k selected by the first multiplexer 81A, via transmission matching elements 82-1, 82-2 and 82-3 for making the respective end portions match the respective transmission capacitive cells 17k. If the three coaxial cables 23-1, 23-2 and 23-3 are employed, as indicated by the alternate long and two short dashes lines, a configuration in which proximal end portions of the coaxial cables 23-1, 23-2 and 23-3 are connected to three transmission circuits 31-1, 31-2 and 31-3 included in the transmission circuit 31, respectively, may be employed. Illustration of capacitors 33a is omitted.

Likewise, the reception capacitive cells 18j (j=a, b, c, ..., n) are connected to, for example, n terminals of a second multiplexer 81B arranged inside the distal end portion 15, and a decoder 84B to which a selection control signal conveyed from the control circuit 36 via the cable 80 is applied is provided in the vicinity of the second multiplexer 81B. The decoder 84B generates selection signals from the applied (inputted) selection control signal, and outputs the generated selection signals to the second multiplexer 81B, and the second multiplexer 81B selects a plurality of (for example, three) reception capacitive cells 18k from the n reception capacitive cells according to the selection signals. The selected three reception capacitive cells 18k receive ultrasound that has radially scanned and generate ultrasound reception signals. As described above, upon an input of a selection control signal, the decoder 84A generates selection signals for selecting a plurality of (three in the specific example) reception capacitive cells 18k used for ultrasound reception, for the second multiplexer 81B.

The ultrasound reception signals generated by the three reception capacitive cells 18k pass through a reception matching element 83 arranged in the vicinity of the reception ultrasound transducer 18, the reception matching element 83 providing matching means (or a matching section), and are conveyed with a DC bias voltage superimposed thereon, via a reception signal cable 26 to a reception circuit 32.

As described above, the reception signal cable 26 conveys the ultrasound reception signals generated by the three transmission capacitive cells 17$k$ selected by the second multiplexer 81B, through the reception matching element 83 to the reception circuit 32 inside the observation apparatus 3.

Note that like the first multiplexer 81A, the second multiplexer 81B sequentially selects three reception capacitive cells 18$k$ according to the order of alignment of the reception capacitive cells 18$j$ in such a manner that the second multiplexer 81B selects reception capacitive cells 18$a$, 18$b$ and 18$c$ according to the selection signals from the decoder 84B in a first clock L level period synchronized with a first reception period of the selection control signal, selects reception capacitive cells 18$b$, 18$c$ and 18$d$ in a second clock L level period, and selects reception capacitive cells 18$c$, 18$d$ and 18$e$ in a third clock L level period. FIG. 8 also illustrate timings for a selection control signal applied (inputted) to the decoder 84B and selection signals outputted from the decoder 84B, for description of operation. The operation in this case is similar to the description related to the decoder 84A in the above-described transmission periods as follows.

As illustrated in the Figure, first, second, . . . , L level clocks are outputted as a selection control signal in synchronization with first, second, . . . reception periods Tr1, Tr2, . . . . The decoder 84B generates three cell selection signals 86$a$, 86$b$ and 86$c$, which provide selection signals, from a falling edge of a clock such as above, and outputs the cell selection signals 86$a$, 86$b$ and 86$c$ to selection control terminals of the second multiplexer 81B.

Upon an input of the first clock of the selection control signal synchronized with the first reception period Tr1, which is a first reception period, the decoder 84B outputs a cell selection signal 86$a$ with only one H level bit as an output value (count value) from a first output end, outputs a cell selection signal 86$b$ with two H level bits (one bit added to one bit from the first output end) as an output value from a second output end, and outputs a cell selection signal 86$c$ with three H level bits (one bit added to two bits from the second output end) as an output value from a third output end, to the selection control terminals of the second multiplexer 81B. The second multiplexer 81B is set so as to select three reception capacitive cells 18$k$ according to the bit counts as outputs values of the cell selection signals 86$a$, 86$b$ and 86$c$ outputted by the decoder 84B. For example, the second multiplexer 81B is set so as to if the bit count Bb of the cell selection signal 86$a$ (or 86$b$ or 86$c$) is Bb=1 bit, selects the reception capacitive cell 18$a$, if Bb=2 bits, select the reception capacitive cell 18$b$, . . . , and if Bb=n bits, selects the reception capacitive cell 18$n$, respectively. Here, reference numeral n indicates the number of reception capacitive cells as described above.

Also, the decoder 84B is set so as to if the bit count Bb reaches Bb=n, reset the bit count Bb to zero immediately before an input of a next (n+1)-th clock, and upon an input of the (n+1)-th clock, output a cell selection signal 86$b$ with one bit again. Accordingly, if the cell selection signals 86$a$, 86$b$, and 86$c$ have one bit, two bits and three bits, respectively, the second multiplexer 81B selects the reception capacitive cells 18$a$, 18$b$ and 18$c$, which is a first, a second and a third in the alignment order.

Also, upon an input of a second clock as a selection control signal synchronized with the second reception period Tr2, the decoder 84B outputs a cell selection signal 86 with two H level bits (one bit added to one bit in the previous period) as an output value from a first output end, outputs a cell selection signal 86$b$ with three H level bits (one bit added to the two bits from the first output end) as an output value from the second output end, and outputs a cell selection signal 86$c$ with four H level bits (one bit added to the three bits from the second output end) as an output value from the third output end, to the second multiplexer 81B. Accordingly, in this case, the second multiplexer 81B selects the reception capacitive cells 18$b$, 18$c$ and 18$d$, which is the second, the third and a fourth in the alignment order. The second multiplexer 81B sequentially selects three reception capacitive cells 18$k$ according to the alignment order.

Then, the selected three reception capacitive cells 18$k$ receive ultrasound that has radially scanned. In the present modification, the reception cell region Rr1 for generating ultrasound reception signals for one pixel includes three reception capacitive cells 18$k$, as in the case of the above-described transmission cell region Rs1, moves according to a direction (or a radial narrow region) in which ultrasound is received, within the reception ultrasound transducer 18 that provides a reception region for ultrasound that radially scans (that is, the n reception capacitive cells 18$a$ to 18$n$). However, a predetermined reception cell region Rr1 is determined according to the direction (or the narrow radial region) in which ultrasound is received. On the other hand, in the first embodiment, the reception cell region Rr remains unchanged even if the direction in which ultrasound changes.

The reception matching element 83 makes impedances of three reception capacitive cells 18$k$ that output ultrasound reception signals match an end portion (entrance end) of the reception signal cable 26 having a second characteristic impedance value Z2 to convey the ultrasound reception signals outputted by the three reception capacitive cells 18$k$ via the reception signal cable 26.

In other words, the reception matching element 83 performs impedance matching for the ultrasound reception signals outputted from the three reception capacitive cells 18$k$ to reduce occurrence of reflection and conveys the resulting ultrasound reception signals to the reception signal cable 26 side. Note that, although in the examplec illustrated in FIG. 7, the impedances of the selected parallelly-connected three reception capacitive cells 18$k$ are matched with the reception signal cable 26 by one reception matching element 83, impedance matching may be performed for each one selected reception capacitive cell 18$k$. Also, if impedance matching is performed for each one reception capacitive cell 18$k$, as illustrated in FIG. 9, the reception signal cable 26 may include three coaxial cables.

As illustrated in FIG. 9, end portions of three coaxial cables 26-1, 26-2 and 26-3 included in the reception signal cable 26 are connected to the respective reception capacitive cells 18$k$ selected by the second multiplexer 81, via reception matching elements 83-1, 83-2 and 83-3, respectively. If the three coaxial cables 26-1, 26-2 and 26-3 are employed, as indicated by the alternate long and two short dashes lines, a configuration in which proximal end portions of the three coaxial cables 26-1, 26-2 and 26-3 are connected to three reception circuits 32-1, 32-2 and 32-3 each provided by a reception circuit 32 may be employed. Illustration of capacitors 33$b$ is omitted.

Note that in FIGS. 7 and 9, the transmission capacitive cells 17$k$ (k=a, b, c) and the reception capacitive cells 18$k$ first selected according to the selection signals are indicated as the transmission cell region Rs1 and the reception cell region Rr1. As described above, the transmission cell region Rs1 and the reception cell region Rr1 for generating one pixel sequentially move according to the selection signals. Then, with obtainment of an ultrasound image for one frame as a cycle, an operation similar to the above is repeated. The rest of the configuration is similar to that of the above-described first embodiment, and a description thereof will be omitted.

Note that an ultrasound tomographic image for one pixel is generated from ultrasound reception signals in a j-th transmission/reception period Tj including a j-th transmission period Tsj and a j-th reception period Trj as described above. Here, j=1, 2, . . . n.

In the present modification, the operation is basically similar to the operation in the first embodiment except that an operation in which mechanical ultrasound scanning is performed in the first embodiment is changed to an operation in which electrical ultrasound scanning is performed. In the present modification, also, if an ultrasound transmission signal superimposed on a DC bias voltage is conveyed from the transmission circuit 31 to three transmission capacitive cells 17a, 17b and 17c via the transmission signal cable 23 in the first transmission period Ts1, the ultrasound transmission signal is applied to the transmission capacitive cells 17a, 17b and 17c included in the transmission ultrasound transducer 17 through the transmission matching element 82 provided at the end portion of the transmission signal cable 23.

In this case, as illustrated in FIG. 7, impedance matching between the end portion of the transmission signal cable 23 and the (parallelly-connected) three transmission capacitive cells 17a, 17b and 17c included in the transmission ultrasound transducer 17 is performed by the transmission matching element 82. Also, in FIG. 9, impedance matching is performed for each of the transmission capacitive cells 17a, 17b and 17c.

Therefore, the ultrasound transmission signal, which is in a nearly ideal state, is applied to the (parallelly-connected) three transmission capacitive cells 17a, 17b and 17c without the ultrasound transmission signal being reflected because of an impedance mismatch, or signal waveform distortion caused as a result of the reflected ultrasound transmission signal being superimposed on the original ultrasound transmission signal. Thus, a decrease in S/N ratio due to signal waveform distortion and occurrence of a decrease in signal level due to reflection of the ultrasound transmission signal can be reduced (or suppressed).

In the first reception period Tr1 following the first transmission period Ts1, ultrasound reception signals outputted from the reception capacitive cells 18a, 18b and 18c are inputted to the end portion of the reception signal cable 26 though the reception matching element 83.

In this case, the impedances of the reception capacitive cells 18a, 18b and 18c and the impedance of the end portion of the reception signal cable 26 are matched by the reception matching element 83, and thus, the ultrasound reception signals are conveyed to the reception signal cable 26 side without signal waveform distortion due to an impedance mismatch. Thus, a decrease in S/N ratio and receiving sensitivity due to signal waveform distortion can be prevented.

The ultrasound reception signals conveyed to the reception signal cable 26 are inputted to the reception circuit 32 via the reception signal cable 26.

The reception circuit 32 performs image processing on the inputted ultrasound signals and stores the resulting image in a memory as first sound-ray data. Upon an end of the first reception period Tr1, a second transmission period Ts2 starts and the switch 34 is switched. Then, the direction in which ultrasound is transmitted/received is slightly different from that in the first transmission period Ts1. The operation in the second transmission period Ts2 is the same as that in the first transmission period Ts1 except the difference in ultrasound transmission direction. Also, the operation in the second reception period Tr2 is the same as that in the first reception period Tr1 except the slight difference in ultrasound reception direction.

Accordingly, the ultrasound diagnostic apparatus 1D in FIG. 7 provides effects substantially similar to those of the first embodiment illustrated in FIG. 1. Although the above description has been provided in terms of a case where three transmission capacitive cells 17k and three reception capacitive cells 18k are selected as an example of selection of a plurality of transmission capacitive cells 17k and a plurality of reception capacitive cells 18k, a number of transmission capacitive cells 17k, the number being one or a plural number other than three, and a number of reception capacitive cells 18k, the number being one or a plural number other than three, may be selected. Also, although the description has been provided in term of radial scanning, scanning in the present invention is not limited to radial scanning, and another type of scanning, for example, convex scanning may be employed.

Also, although the present modification described with reference to FIGS. 7 to 9 has been described in terms of a case where electronic scanning is employed in the first embodiment in FIG. 1, the present modification can be applied to any of the other embodiments and the like.

Figure 10:
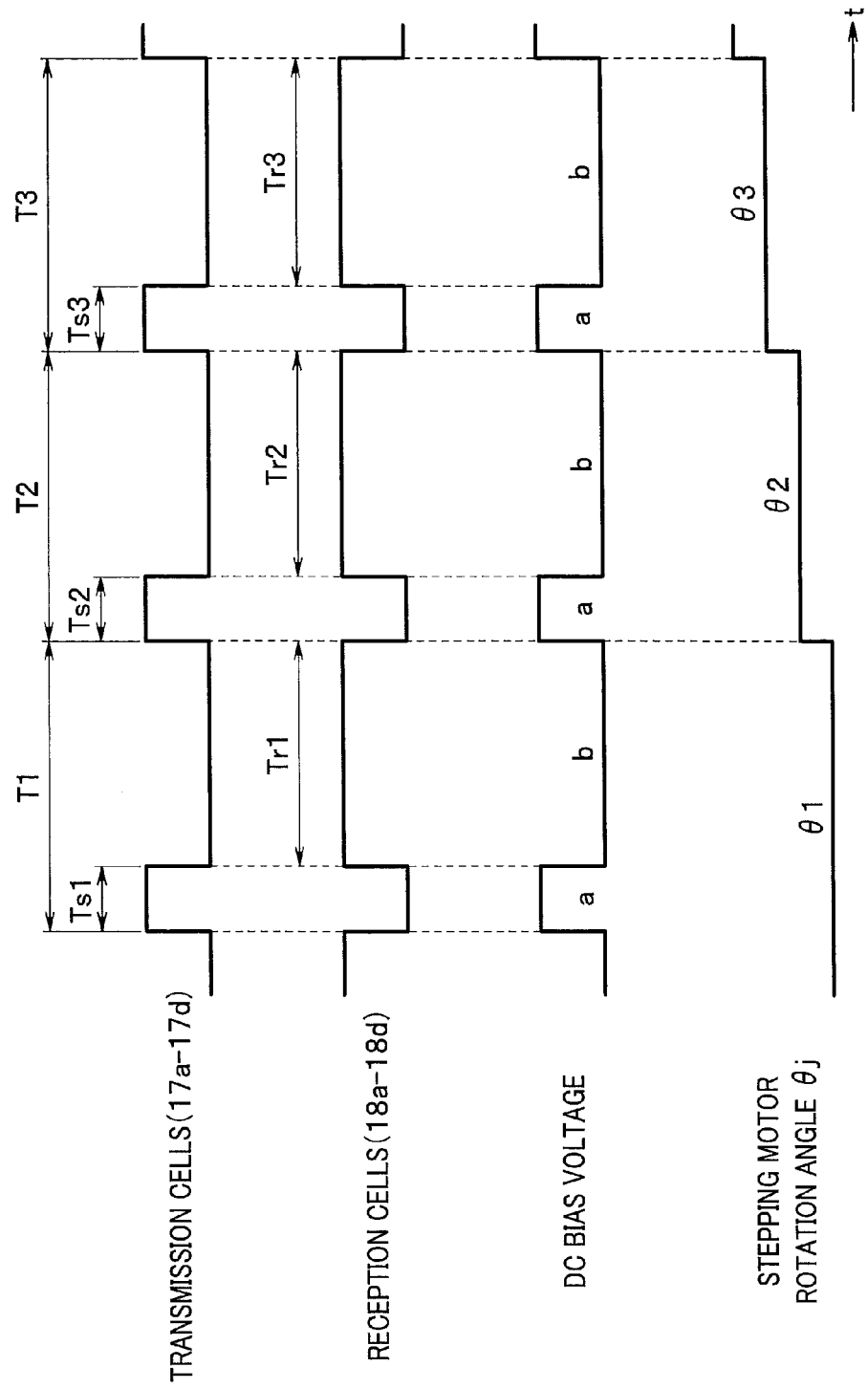
FIG. 10 is a timing chart for a case where a rotation angle of a stepping motor is synchronized with each ultrasound transmission/reception period for one pixel in the first embodiment.

Also, mechanical scanning in the first embodiment may be performed as the follows. In the case of mechanical scanning in the first embodiment, as the motor in the rotation driving section 21, a stepping motor 21a (indicated by the dotted lines in FIG. 1) that rotates a step-like manner each time a transmission period Tsj for one pixel using the four transmission capacitive cells 17a to 17d and a reception period Trj for one pixel using the four reception capacitive cells 18a to 18d have passed may be used. FIG. 10 illustrates ultrasound transmission/reception periods Tj for one pixel each including a transmission period Tsj for one pixel and a reception period Trj for one pixel and timings of changes in rotation angle θj of the stepping motor 21a. Note that each of the ultrasound transmission/reception periods Tj for one pixel corresponds to a period in which one pixel is generated in a period in which an ultrasound tomographic image for one frame is generated.

As illustrated in FIG. 10, in a same ultrasound transmission/reception period Tj for one pixel, the rotation angle θj of the stepping motor 21a does not change, and thus, reflected signals for one pixel, which result from ultrasound from the four transmission capacitive cells 17a to 17d being reflected, can efficiently be received by the four reception capacitive cells 18a to 18d arranged adjacent to the transmission capacitive cells 17a to 17d. In other words, the effect of providing a large S/N ratio at the time of reception can be provided. Note that in FIG. 10, the transmission capacitive cells and the reception capacitive cells are abbreviated as transmission cells and reception cells, respectively. The transmission capacitive cells 17a to 17d and the reception capacitive cells 18a to 18d operate in transmission periods Tsj and reception periods Trj, which are indicated as being of an H level, respectively.

Also, a DC bias voltage provided by the DC bias generation circuit 35 is alternately switched between the transmission periods Tsj and the reception periods Trj. In FIG. 10, symbol a indicates a period in which a DC bias voltage is applied to the transmission capacitive cells 17a to 17d and symbol b indicates a period in which the DC bias voltage is applied to the reception capacitive cells 18a to 18d. Also, for example, a configuration in which, as indicated by the dotted lines, capacity-variable capacitors 53a and 56a each including, e.g., a trimmer capacitor whose capacity can be varied are connected in parallel to the capacitors 53 and 54 illustrated in FIG. 3, enabling adjustment of impedances of the transmission matching element 22 and the reception matching element 25, may be employed. In other words, a first matching section that performs matching for a transmission signal may include a first element having a predetermined impedance value and a second element having a variable impedance value, and a second matching section that performs matching for reception signals may include a third element having a predetermined impedance value and a fourth element having a variable impedance value.

With such configuration, even if the impedances of the transmission capacitive cells 17a to 17d and the reception capacitive cells 18a to 18d change over time, the impedances of the transmission matching element 22 and the reception matching element 25 can easily be adjusted by making the trimmer capacitors each have a variable capacitance so that impedance matching can be maintained.

If the impedances of the transmission capacitive cells 17a to 17d and the reception capacitive cells 18a to 18d change over time, a mismatch occurs when a transmission signal is conveyed from the transmission signal cable 23a to the transmission capacitive cells 17a to 17d or if reception signals are conveyed from the reception capacitive cells 18a to 18d to the reception signal cable 26a; however, making the capacitances of the trimmer capacitors variable facilitates easy matching.

Also, for example, if there are individual differences in impedance (capacity) among the transmission capacitive cells 17a to 17d and the reception capacitive cells 18a to 18d used in a product, the differences among the respective products can be absorbed using the common transmission matching element 22 and the common reception matching element 25, by means of adjustment at the trimmer capacitor parts. Note that the elements each having a variable capacitance using trimmer capacitors, which are illustrated in FIG. 3, may be employed in any of the embodiments other than the embodiment in FIG. 3. For example, the transmission matching element 22 having a trimmer capacitor can be employed in FIG. 4, and also can be employed in each of the transmission matching elements 22a to 22d in FIG. 5, the transmission matching elements 22a and 22c in FIG. 6, the transmission matching element 82 in FIG. 7 and the transmission matching elements 82-1 to 82-3 in FIG. 9, and can also be employed in the second transmission matching element 61 in FIG. 4.

Also, for example, the reception matching element 25 including a trimmer capacitor can be employed in FIG. 4, can also be employed for each of the reception matching elements 25a to 25d in FIG. 5, the reception matching elements 25b and 25d in FIG. 6, the reception matching element 83 in FIG. 7 and the reception matching elements 83-1 to 83-3 in FIG. 9, and can also be employed for the second reception matching element 62 in FIG. 4.

Also, for example, in a matched state in which the transmission ultrasound transducer 17 and the reception ultrasound transducer 18 illustrated in FIG. 4 are matched with the transmission signal cable 23a and the reception signal cable 26a by the transmission matching element 22 and the reception matching element 25, respectively, a reference waveform obtained in advance by ultrasound being transmitted/received to/from a reference ultrasound target object and a threshold waveform that is a tolerance limit of deviation from the reference waveform, the threshold waveform being obtained by providing a mismatch state by means of, e.g., changing a capacitance value of a trimmer capacitor in a matched state, may be obtained in advance and stored in a storage section such as a non-volatile memory. Then, it is possible that after use of the ultrasound endoscope 2 over an arbitrary period of time, using the aforementioned reference ultrasound target object, ultrasound is transmitted/received to/from the reference ultrasound target object to determine whether or not the resulting waveform is one in a tolerable range by comparing the waveform with the reference waveform or the threshold waveform stored in the storage section, enabling determination of whether or not the matched state is maintained and whether or not the ultrasound endoscope 2 departs from the tolerable control state range because of, e.g., secular change.

Note that for the reference ultrasound target object, for example, an object that reflects ultrasound only at (one or more) position(s) with a certain distance from the transmission capacitive cells 17a to 17d and the reception capacitive cells 18a to 18d, and does not reflect the ultrasound at the positions with other distances from the same is provided. In a mismatch state, a signal level of a signal from the position(s) with the certain distance decreases, the signal levels of signals from the positions with the other distances increase because of the mismatch, and thus, whether or not a matched state is maintained can be determined by, e.g., waveform comparison or signal level comparison.

Thus, in the observation apparatus 3 in FIG. 1, the storage section 40 (indicated by the dotted lines) that stores a reference waveform and a threshold waveform measured for a reference ultrasound target object in a matched state using the ultrasound endoscope 2 or signal level(s) at position(s) with representative distance(s) for the reference waveform or the threshold waveform, in association with the ultrasound endoscope 2 used for the measurement may be provided.

Then, when a measured waveform measured using the reference ultrasound target object is displayed on the first monitor 4, the control circuit 36 performs control to display, e.g., the reference waveform stored in the storage section 40 in such a manner that the measured waveform can be compared with the reference waveform or the measured waveform and the reference waveform are displayed in an overlapped manner with difference display colors on the first monitor 4.

A user can easily determine whether or not a matched state is maintained, from the measured waveform and the reference waveform or the like displayed on the first monitor 4. Also, the control circuit 36 may have a function of a determination section 36a (indicated by the dotted lines) that determines whether the measured waveform falls within a tolerable matched state range within the threshold waveform or the measured waveform indicates a mismatch state departing from the threshold waveform, by comparing the measured waveform and the reference waveform or the like.

In other words, the following configurations may be added. The storage section 40 that stores in advance information on a reference signal level and a threshold signal level for at least a representative distance for a reference waveform of an ultrasound reception signal obtained for a reference ultrasound target object that is a reference, with the first matching section and the second matching section set to provide a matched state, and a threshold waveform obtained when a mismatch that the reference waveform is shifted from the matched state to a tolerance limit is provided, and the determination section 36a that determines whether or not the first matching section and the second matching section each provide a matched state by comparison between a signal level of an ultrasound reception signal obtained when ultrasound is transmitted/received to/from the reference ultrasound target object and the reference signal level and the threshold signal level read from the storage section may be provided. Note that the determination section 36a may include, e.g., a comparison circuit provided outside the control circuit 36.

Also, only one of the information on the reference waveform and the information on the threshold waveform may be stored in the storage section 40.

Also, instead of provision of the storage section 40 in the observation apparatus 3, an identification information storage section that stores identification information unique to the ultrasound endoscope 2 may be provided inside the connector 7 of the ultrasound endoscope 2 in FIG. 1 to store the information to be stored in the storage section 40, in the identification information storage section. Then, for example, the control circuit 36 may perform control as in the case of the storage section 40. Also, although the configuration provided with, e.g., the storage section 40 is illustrated in the ultrasound diagnostic apparatus 1 in FIG. 1, the storage section 40 may be provided in any of FIGS. 2, 4, 5, 6 and 7.

Also, embodiments configured by partially combining the above-described embodiments and the like also belong to the present invention. For example, an embodiment with positions of the matching sections changed also belongs to the present invention.

Also, in the present invention, not all the components disclosed in the present description are components necessary for the present invention, and the components of the present invention described in claim 1 may be considered as minimum necessary components for the present invention. Furthermore, a configuration in which one or more components in the description or any of the claims other than claim 1 are arbitrarily or selectively added to the minimum necessary components may be employed.

What is claimed is:

1. An ultrasound diagnostic apparatus comprising:
an ultrasound probe including a capacitive micromachined ultrasound transducer;
an ultrasound observation apparatus to which the ultrasound probe is detachably connected, the ultrasound observation apparatus including a transmission circuit that generates an ultrasound transmission signal for sending ultrasound out from the capacitive micromachined ultrasound transducer, and a reception circuit that performs signal processing on an ultrasound reception signal generated as a result of ultrasound being received by the capacitive micromachined ultrasound transducer;
a transmission ultrasound transducer and a reception ultrasound transducer included in the capacitive micromachined ultrasound transducer, the transmission ultrasound transducer including a plurality of transmission capacitive cells that send out ultrasound for generating an ultrasound beam for one pixel, and the reception ultrasound transducer including a plurality of reception capacitive cells that receive reflected ultrasound of the sent-out ultrasound and output an ultrasound reception signal for one pixel;
a transmission signal cable connecting the transmission ultrasound transducer and the transmission circuit in the ultrasound observation apparatus;
a reception signal cable connecting the reception ultrasound transducer and the reception circuit in the ultrasound observation apparatus;
a DC bias voltage applying circuit provided in the ultrasound observation apparatus, the DC bias voltage applying circuit applying a DC bias voltage to an input-side end portion of the transmission signal cable that transmits the ultrasound transmission signal and applying the DC bias voltage to an output-side end portion of the reception signal cable that transmits the ultrasound reception signal; and
at least one first matching section and at least one second matching section configured to perform electrical impedance matching for the ultrasound transmission signal on which the DC bias voltage is superimposed and conveyed via the transmission signal cable and the ultrasound reception signal on which the DC bias voltage is superimposed and conveyed via the reception signal cable, respectively,
wherein the plurality of transmission capacitive cells are arranged in a transmission region, and the plurality of reception capacitive cells are arranged in a reception region adjacent to the transmission region, and the first matching section is provided in the transmission region and the second matching section is provided in the reception region and
wherein the first matching section includes:
first and second coils that connect in series an end portion of a center conductor of a first coaxial cable constituting the transmission signal cable, the center conductor transmitting the ultrasound transmission signal on which the DC bias voltage is superimposed, to an electrode on one side of the plurality of transmission capacitive cells,
a first capacitor having opposite ends respectively connected with a point of connection between the first and second coils, and an electrode on another side of the plurality of transmission capacitive cells, the electrode being connected with an end portion of an outer conductor of the first coaxial cable, and
a first trimmer capacitor connected in parallel with the first capacitor, the first trimmer capacitor having a capacitance value that is adjustable, and wherein the second matching section includes:
third and fourth coils that connect in series an end portion of a center conductor of a second coaxial cable constituting the reception signal cable, the center conductor transmitting the ultrasound reception signal on which the DC bias voltage is superimposed, to an electrode on one side of the plurality of reception capacitive cells,
a second capacitor having opposite ends respectively connected with a point of connection between the third and fourth coils and an electrode on another side of the plurality of reception capacitive cells, the electrode being connected with an end portion of an outer conductor of the second coaxial cable, and
a second trimmer capacitor connected in parallel with the second capacitor, the second trimmer capacitor having a capacitance value that is adjustable.

2. The ultrasound diagnostic apparatus according to claim 1, wherein the first matching section is provided for the plurality of transmission capacitive cells in the transmission region.

3. The ultrasound diagnostic apparatus according to claim 1, wherein the second matching section is provided for the plurality of reception capacitive cells in the reception region.

4. The ultrasound diagnostic apparatus according to claim 2, wherein the second matching section is provided for the plurality of reception capacitive cells in the reception region.

5. The ultrasound diagnostic apparatus according to claim 1, wherein the first matching section is provided at a peripheral portion of the plurality of transmission capacitive cells and an output-side end portion of the transmission signal cable.

6. The ultrasound diagnostic apparatus according to claim 3, wherein the second matching section is provided at a peripheral portion of the plurality of reception capacitive cells and an input-side end portion of the reception signal cable.

7. The ultrasound diagnostic apparatus according to claim 1, further comprising a third matching section configured to perform electrical impedance matching when the ultrasound transmission signal generated by the transmission circuit is conveyed via the transmission signal cable on an output end of the transmission circuit in the ultrasound observation apparatus and the input-side end portion of the transmission signal cable.

8. The ultrasound diagnostic apparatus according to claim 1, further comprising a fourth matching section configured to perform electrical impedance matching when the ultrasound reception signal conveyed via the reception signal cable is inputted to the reception circuit on the output-side end portion of the reception signal cable and an input end of the reception circuit in the ultrasound observation apparatus.

9. The ultrasound diagnostic apparatus according to claim 1, wherein the transmission region and the reception region are included in a same region, and the plurality of transmission capacitive cells and the plurality of reception capacitive cells are mixed in the same region set as a region where ultrasound for generating an ultrasound beam for one pixel is transmitted and received.

10. The ultrasound diagnostic apparatus according to claim 1,
wherein the first matching section includes a first element having a predetermined impedance value and a second element having a variable impedance value; and
wherein the second matching section includes a third element having a predetermined impedance value and a fourth element having a variable impedance value.

11. The ultrasound diagnostic apparatus according to claim 10, wherein the second element and the fourth element each include a trimmer capacitor having a variable capacitance value.

12. The ultrasound diagnostic apparatus according to claim 1,
wherein the ultrasound probe includes an electronic scanning-type capacitive micromachined ultrasound transducer that includes M pieces of the transmission capacitive cells including N pieces of the transmission capacitive cells and M pieces of the reception capacitive cells including N pieces of the reception capacitive cells, the transmission capacitive cells and the reception capacitive cells being arranged along a circumferential direction of a distal end portion of an elongated insertion portion, the electronic scanning-type capacitive micromachined ultrasound transducer sequentially and electrically selecting N pieces of the transmission capacitive cells from M pieces of the transmission capacitive cells and N pieces of the reception capacitive cells from M pieces of the reception capacitive cells, and causing the transmission capacitive cells and the reception capacitive cells to operate for transmission and reception, respectively;
wherein the first matching section performs electrical impedance matching when the ultrasound transmission signal is conveyed to the N pieces of transmission capacitive cells arranged in the predetermined transmission region from the transmission signal cable; and
wherein the second matching section performs electrical impedance matching when the ultrasound reception signal is conveyed from the N pieces of reception capacitive cells arranged in the predetermined reception region to the reception signal cable.

13. The ultrasound diagnostic apparatus according to claim 12,
wherein the first matching section includes a first element having a predetermined impedance value, and a second element having a variable impedance value; and
wherein the second matching section includes a third element having a predetermined impedance value and a fourth element having a variable impedance value.

14. The ultrasound diagnostic apparatus according to claim 1, further comprising:
a storage device configured to store in advance information on a reference signal level and a threshold signal level for at least a representative distance for a reference waveform of an ultrasound reception signal obtained for a reference ultrasound target object that is a reference, with the first matching section and the second matching section set to provide a matched state, and a threshold waveform obtained when a mismatch that the reference waveform is shifted from the matched state to a tolerance limit is provided; and
a determination circuit configured to determine whether or not the first matching section and the second matching section each provide a matched state by comparison between a signal level of an ultrasound reception signal obtained when ultrasound is transmitted to and received from the reference ultrasound target object and the reference signal level and the threshold signal level read from the storage section.

15. The ultrasound diagnostic apparatus according to claim 1, wherein the transmission signal cable is constituted by a first coaxial cable, and the reception signal cable is constituted by a second coaxial cable different from the first coaxial cable, and wherein the DC bias voltage applying circuit includes:
a DC bias voltage generation circuit that generates the DC bias voltage, and
a change-over switch which, during a transmission period in which the ultrasound transmission signal is transmitted, switches such that the DC bias voltage generated by the DC bias voltage generation circuit is applied between a center conductor and an outer conductor of the first coaxial cable, and during a reception period in which the ultrasound reception signal is transmitted, switches such that the DC bias voltage generated by the DC bias voltage generation circuit is applied between a center conductor and an outer conductor of the second coaxial cable.

* * * * *